United States Patent
Policker et al.

(10) Patent No.: US 8,417,329 B2
(45) Date of Patent: Apr. 9, 2013

(54) ANALYSIS AND REGULATION OF FOOD INTAKE

(75) Inventors: Shal Policker, Tenafly, NJ (US); Aharon Grossman, Durham, NC (US); Anat Kliger, Tel-Aviv (IL)

(73) Assignee: Metacure Ltd., Hamilton (BM)

( * ) Notice: Subject to any disclaimer, the term of this patent is extended or adjusted under 35 U.S.C. 154(b) by 0 days.

(21) Appl. No.: 12/599,350

(22) PCT Filed: May 11, 2008

(86) PCT No.: PCT/IL2008/000646
§ 371 (c)(1),
(2), (4) Date: Jun. 7, 2010

(87) PCT Pub. No.: WO2008/139463
PCT Pub. Date: Nov. 20, 2008

(65) Prior Publication Data
US 2010/0305468 A1    Dec. 2, 2010

Related U.S. Application Data

(60) Provisional application No. 60/916,919, filed on May 9, 2007, provisional application No. 61/051,901, filed on May 9, 2008.

(51) Int. Cl.
*A61B 5/05* (2006.01)
*A61F 2/00* (2006.01)
*A61F 13/00* (2006.01)
*A61N 1/00* (2006.01)
(52) U.S. Cl. .............................. 600/547; 600/37; 607/40
(58) Field of Classification Search .................... 607/40, 607/62, 133; 600/37, 547, 593
See application file for complete search history.

(56) References Cited

U.S. PATENT DOCUMENTS

| | | | |
|---|---|---|---|
| 3,411,507 A | 11/1968 | Wingrove | |
| 4,133,315 A | 1/1979 | Berman et al. | |

(Continued)

FOREIGN PATENT DOCUMENTS

| | | |
|---|---|---|
| EP | 1 036 545 | 9/2000 |
| WO | WO 97/25098 | 7/1997 |

(Continued)

OTHER PUBLICATIONS

An abstract entitled "Gastric myoelectrical pacing as therapy for morbid obesity: Preliminary results", by Cigaina, et al., Dec. 24, 2000.

(Continued)

*Primary Examiner* — Charles A Marmor, II
*Assistant Examiner* — Kaylee Wilson
(74) *Attorney, Agent, or Firm* — William H. Dippert; Eckert Seamans Cherin & Mellott, LLC

(57) ABSTRACT

Apparatus (18, 18') is provided, which includes one or more fundic sensors (74), configured to be applied to a fundus of a subject (10), and to generate a fundic signal. The apparatus further includes a control unit (90), which is configured to make a tentative determination of ingestion by the subject (10), determine fundic impedance responsively to the fundic signal, and calculate a duration of a period during which the fundic impedance rose during the tentatively-determined ingestion. Upon finding that the duration is less than a fundic rise duration threshold value, the control unit (90) determines that the tentative determination of ingestion is a false positive. Other embodiments are also described.

31 Claims, 14 Drawing Sheets

U.S. PATENT DOCUMENTS

| | | | |
|---|---|---|---|
| 4,416,267 A | 11/1983 | Garren et al. |
| 4,592,339 A | 6/1986 | Kuzmak |
| 4,823,808 A | 4/1989 | Clegg et al. |
| 4,975,682 A | 12/1990 | Kerr et al. |
| 5,074,868 A | 12/1991 | Kuzmak |
| 5,188,104 A | 2/1993 | Wernicke et al. |
| 5,226,429 A | 7/1993 | Kuzmak |
| 5,231,988 A | 8/1993 | Wernicke et al. |
| 5,234,454 A | 8/1993 | Bangs |
| 5,263,480 A | 11/1993 | Wernicke et al. |
| 5,292,344 A | 3/1994 | Douglas |
| 5,314,458 A | 5/1994 | Najafi et al. |
| 5,363,103 A | 11/1994 | Inkol |
| 5,423,872 A | 6/1995 | Cigaina |
| 5,449,368 A | 9/1995 | Kuzmak |
| 5,601,604 A | 2/1997 | Vincent |
| 5,658,298 A | 8/1997 | Vincent et al. |
| 5,690,691 A | 11/1997 | Chen et al. |
| 5,692,501 A | 12/1997 | Minturn |
| 5,716,385 A | 2/1998 | Mittal et al. |
| 5,836,994 A | 11/1998 | Bourgeois |
| 5,861,014 A | 1/1999 | Familoni |
| 5,868,141 A | 2/1999 | Ellias |
| 5,891,185 A | 4/1999 | Freed et al. |
| 5,938,669 A | 8/1999 | Klaiber et al. |
| 5,979,449 A | 11/1999 | Steer |
| 5,995,872 A | 11/1999 | Bourgeois |
| 6,026,326 A | 2/2000 | Bardy |
| 6,067,991 A | 5/2000 | Forsell |
| 6,091,992 A | 7/2000 | Bourgeois et al. |
| 6,104,955 A | 8/2000 | Bourgeois |
| 6,129,685 A | 10/2000 | Howard |
| 6,185,452 B1 | 2/2001 | Schulman et al. |
| 6,210,347 B1 | 4/2001 | Forsell |
| 6,270,455 B1 | 8/2001 | Brown |
| 6,415,178 B1 | 7/2002 | Ben-Haim et al. |
| 6,453,907 B1 | 9/2002 | Forsell |
| 6,454,699 B1 | 9/2002 | Forsell |
| 6,460,543 B1 | 10/2002 | Forsell |
| 6,511,490 B2 | 1/2003 | Robert |
| 6,516,227 B1 | 2/2003 | Meadows et al. |
| 6,547,801 B1 | 4/2003 | Dargent et al. |
| 6,571,127 B1 | 5/2003 | Ben-Haim et al. |
| 6,600,953 B2 | 7/2003 | Flesler et al. |
| 6,735,477 B2 | 5/2004 | Levine |
| 7,006,871 B1 | 2/2006 | Darvish et al. |
| 7,009,511 B2 | 3/2006 | Mazar et al. |
| 7,343,201 B2 | 3/2008 | Mintev |
| 7,359,751 B1 | 4/2008 | Erickson et al. |
| 7,502,649 B2 | 3/2009 | Ben-Haim et al. |
| 7,775,993 B2 | 8/2010 | Heruth et al. |
| 2001/0011543 A1 | 8/2001 | Forsell |
| 2002/0103424 A1 | 8/2002 | Swoyer et al. |
| 2002/0161414 A1 | 10/2002 | Flesler et al. |
| 2002/0165589 A1 | 11/2002 | Imran et al. |
| 2003/0009202 A1 | 1/2003 | Levin |
| 2003/0055464 A1 | 3/2003 | Darvish et al. |
| 2003/0055465 A1 | 3/2003 | Ben-Haim et al. |
| 2003/0055467 A1 | 3/2003 | Ben-Haim et al. |
| 2003/0066536 A1 | 4/2003 | Forsell |
| 2003/0114899 A1 | 6/2003 | Woods et al. |
| 2003/0208212 A1 | 11/2003 | Cigaina |
| 2003/0208242 A1 | 11/2003 | Harel et al. |
| 2004/0044376 A1 | 3/2004 | Flesler et al. |
| 2004/0059393 A1 | 3/2004 | Policker et al. |
| 2004/0088023 A1 | 5/2004 | Imran et al. |
| 2004/0098068 A1 | 5/2004 | Carbunaru et al. |
| 2004/0106963 A1 | 6/2004 | Tsukamoto et al. |
| 2004/0147816 A1* | 7/2004 | Policker et al. ............... 600/300 |
| 2004/0167583 A1 | 8/2004 | Knudson et al. |
| 2004/0249421 A1 | 12/2004 | Harel et al. |
| 2005/0021101 A1 | 1/2005 | Chen et al. |
| 2005/0096514 A1 | 5/2005 | Starkebaum |
| 2005/0164925 A1 | 7/2005 | Jakubowski et al. |
| 2005/0222638 A1 | 10/2005 | Foley et al. |
| 2006/0064037 A1 | 3/2006 | Shalon et al. |
| 2006/0074459 A1 | 4/2006 | Flesler et al. |
| 2006/0085045 A1 | 4/2006 | Harel et al. |
| 2006/0173238 A1 | 8/2006 | Starkebaum |
| 2006/0184207 A1 | 8/2006 | Darvish et al. |
| 2006/0264699 A1 | 11/2006 | Gertner |
| 2007/0027493 A1 | 2/2007 | Ben-Haim et al. |
| 2007/0051849 A1 | 3/2007 | Watts et al. |
| 2007/0060812 A1 | 3/2007 | Harel et al. |
| 2007/0060971 A1 | 3/2007 | Glasberg et al. |
| 2007/0092446 A1 | 4/2007 | Haddad et al. |
| 2007/0156177 A1 | 7/2007 | Harel et al. |
| 2007/0179556 A1 | 8/2007 | Ben-Haim et al. |
| 2007/0185540 A1 | 8/2007 | Ben-Haim et al. |
| 2007/0299320 A1 | 12/2007 | Policker et al. |
| 2008/0046062 A1 | 2/2008 | Camps et al. |
| 2008/0058889 A1 | 3/2008 | Ben-Haim et al. |
| 2008/0058891 A1 | 3/2008 | Ben-Haim et al. |
| 2008/0065168 A1 | 3/2008 | Bitton et al. |
| 2008/0097188 A1 | 4/2008 | Pool et al. |
| 2008/0178684 A1 | 7/2008 | Spehr |
| 2009/0062893 A1 | 3/2009 | Spehr et al. |
| 2009/0088816 A1 | 4/2009 | Harel et al. |
| 2009/0118797 A1 | 5/2009 | Kliger et al. |
| 2009/0131993 A1 | 5/2009 | Rousso et al. |
| 2009/0204063 A1 | 8/2009 | Policker et al. |
| 2009/0281449 A1 | 11/2009 | Thrower et al. |
| 2010/0228105 A1 | 9/2010 | Policker et al. |
| 2010/0305468 A1 | 12/2010 | Policker et al. |
| 2010/0324644 A1 | 12/2010 | Levi et al. |

FOREIGN PATENT DOCUMENTS

| | | |
|---|---|---|
| WO | WO 97/41921 | 11/1997 |
| WO | WO 98/10830 | 3/1998 |
| WO | WO 99/03533 | 1/1999 |
| WO | WO 00/53257 | 9/2000 |
| WO | WO 01/10375 | 2/2001 |
| WO | WO 01/41671 | 6/2001 |
| WO | WO 01/66183 | 9/2001 |
| WO | WO 01/83019 | 11/2001 |
| WO | WO 01/91854 | 12/2001 |
| WO | WO02/26101 | 4/2002 |
| WO | WO 02/38217 | 5/2002 |
| WO | WO 02/053093 | 7/2002 |
| WO | WO 02/082968 | 10/2002 |
| WO | WO 03/045493 | 6/2003 |
| WO | WO 2004/021858 | 3/2004 |
| WO | WO 2004/112563 | 12/2004 |
| WO | WO 2004/112883 | 12/2004 |
| WO | WO 2005/007232 | 1/2005 |
| WO | WO 2005007232 A2 * | 1/2005 |
| WO | WO 2005/023081 | 3/2005 |
| WO | WO 2005/087310 | 9/2005 |
| WO | WO 2006/018851 | 2/2006 |
| WO | WO 2006018851 A2 * | 2/2006 |
| WO | WO 2006/045075 | 4/2006 |
| WO | WO 2006/073671 | 7/2006 |
| WO | WO 2006/087712 | 8/2006 |
| WO | WO 2006/087717 | 8/2006 |
| WO | WO 2006/097934 | 9/2006 |
| WO | WO 2006/102626 | 9/2006 |
| WO | WO 2006/129321 | 9/2006 |
| WO | WO 2006/118790 | 11/2006 |
| WO | WO 2006/119467 | 11/2006 |
| WO | WO 2006/129321 | 12/2006 |
| WO | WO 2007/080595 | 7/2007 |
| WO | WO 2008/117296 | 10/2008 |
| WO | WO 2008/139463 | 11/2008 |
| WO | WO 2011/092710 | 8/2011 |

OTHER PUBLICATIONS

An abstract entitled "Implantable gastric stimulator (IGS) as therapy for morbid obesity: Equipment, surgical technique and stimulation parameters", by Cigaina, et al., Dec. 24, 2000.

Stein et al., "Carrots and sticks: Impact of an incentive/disincentive employee flexible credit benefit plan on health status and medical costs", American Journal of Health Promotion, May/Jun. 1999, V5, I13, 5.

Giuffrida, "Should we pay the patient? Review of financial incentives to enhance patient compliance", Biomedical Journal, vol. 315, pp. 703-707, 1997.

A Supplementary European Search Report dated Aug. 5, 2010, which issued during the prosecution of Applicant's European Patent Application No. 04745004.

An Examination Report dated Apr. 7, 2009, which issued during the prosecution of Applicant's European Patent Application No. EP 06 74 8690.

An International Search Report and a Written Opinion, both date Oct. 28, 2008, which issued during the prosecution of Applicant's PCT/IL08/00646.

A Supplementary Partial European Search Report dated Feb. 20, 2009, which issued during the prosecution of Applicant's European Patent Application No. EP 02 72 7012.

Shai Policker, et al., "Electrical Stimulation of the Gut for the Treatment of Type 2 Diabetes: The Role of Automatic Eating Detection", Journal of Diabetes Science and Technology, vol. 2, Issue 5, Sep. 2008.

USPTO Office Action dated Oct. 28, 2011 in U.S. Appl. No. 12/256,819.

Supplemental European Search Report and Opinion dated Dec. 27, 2011 in EP 06711180.

An Office Action dated Feb. 1, 2012, which issued during the prosecution of U.S. Appl. No. 11/915,647.

An Office Action dated May 10, 2012, which issued during the prosecution of U.S. Appl. No. 11/915,647.

An Office Action dated May 10, 2012, which issued during the prosecution of U.S. Appl. No. 10/599,015.

An Examination Report Dated May 14, 2012, which issued during the prosecution of European Patent Application No. 10188632.3.

An Extended European Search Report Dated Feb. 18, 2011, which issued during the prosecution of European Patent Application No. 10188632.3.

International Search Report and the Written Opinion Dated Sep. 2, 2011 From the International Searching Authority Re. Application No. PCT/IL 11/00116.

* cited by examiner

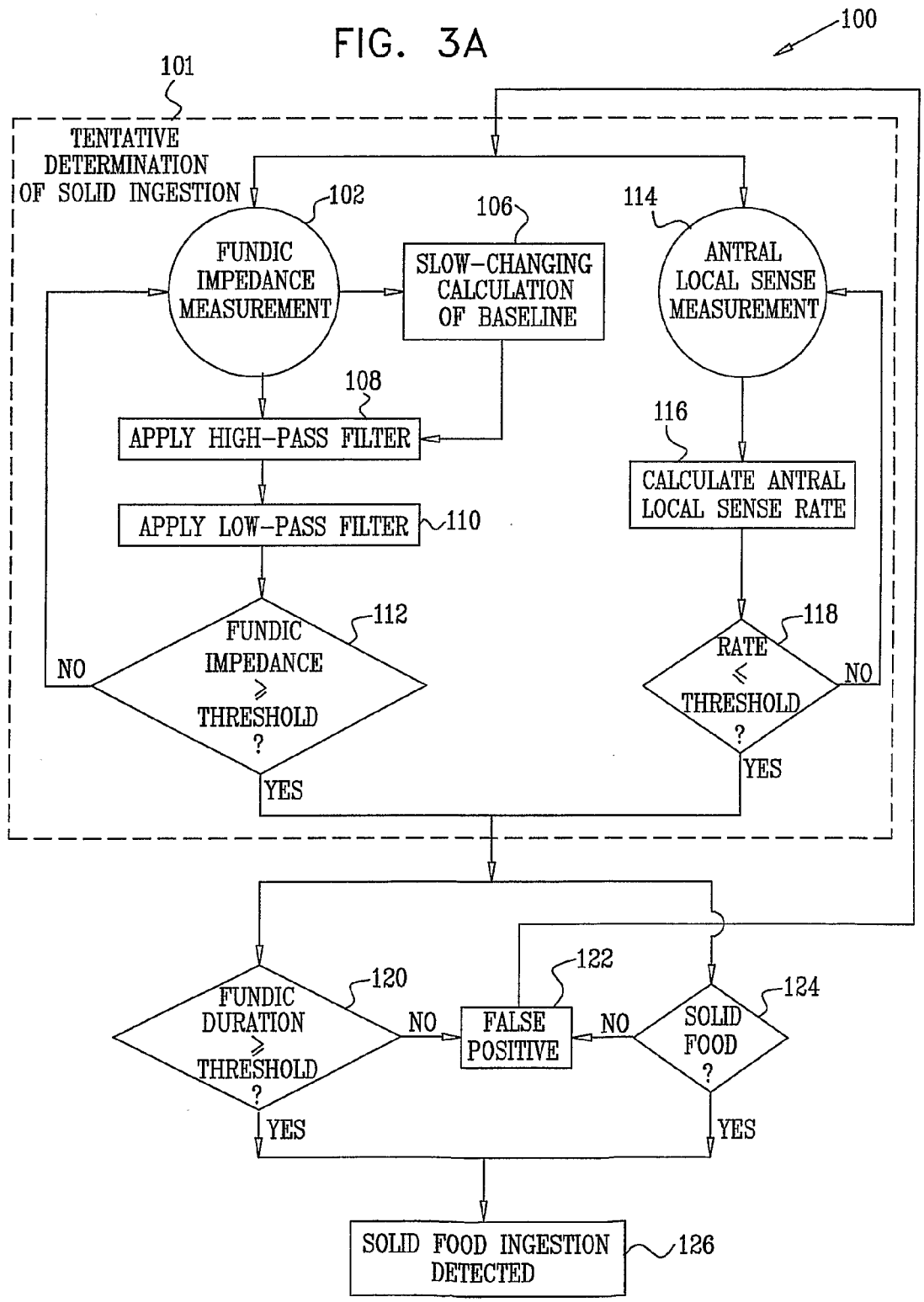

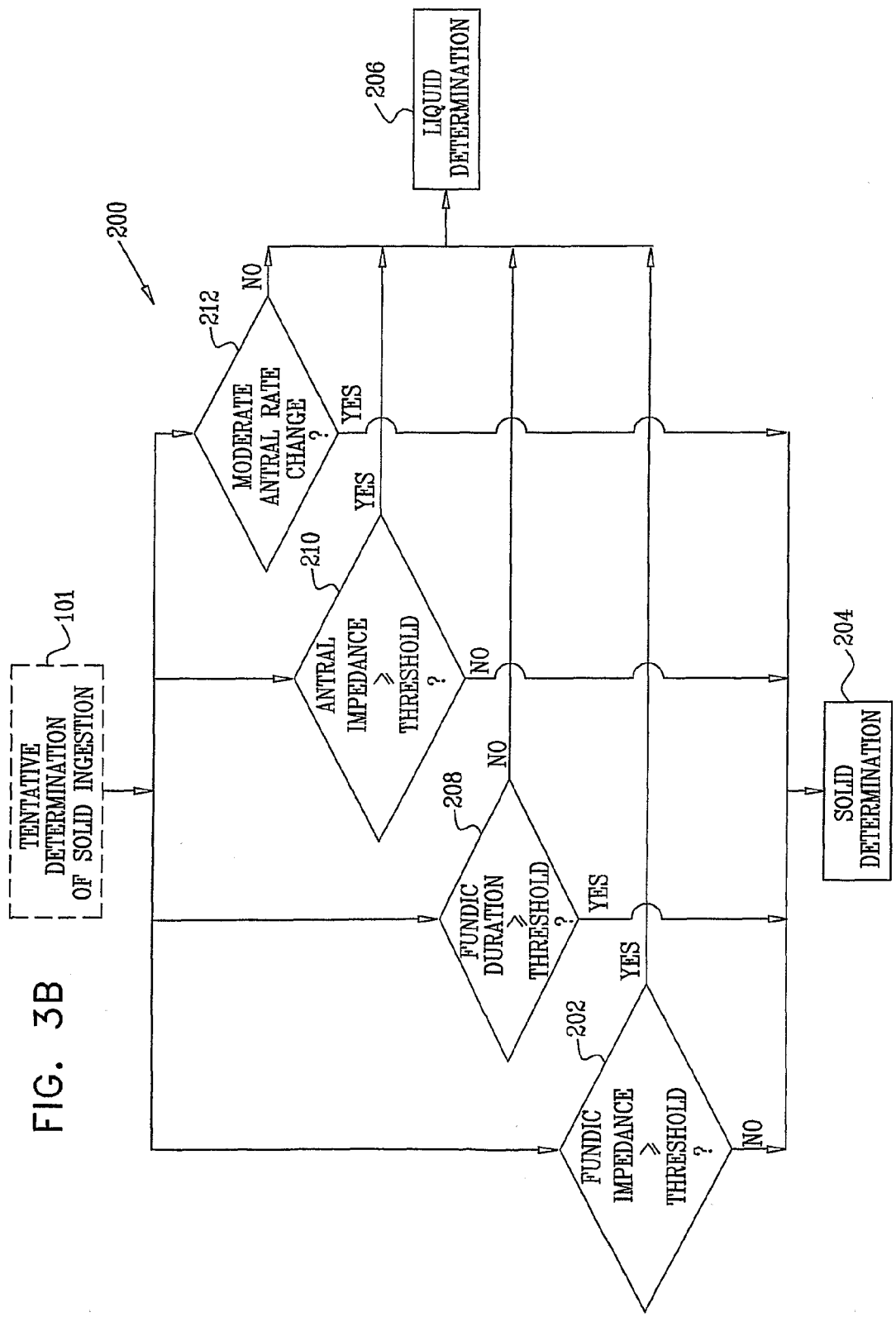

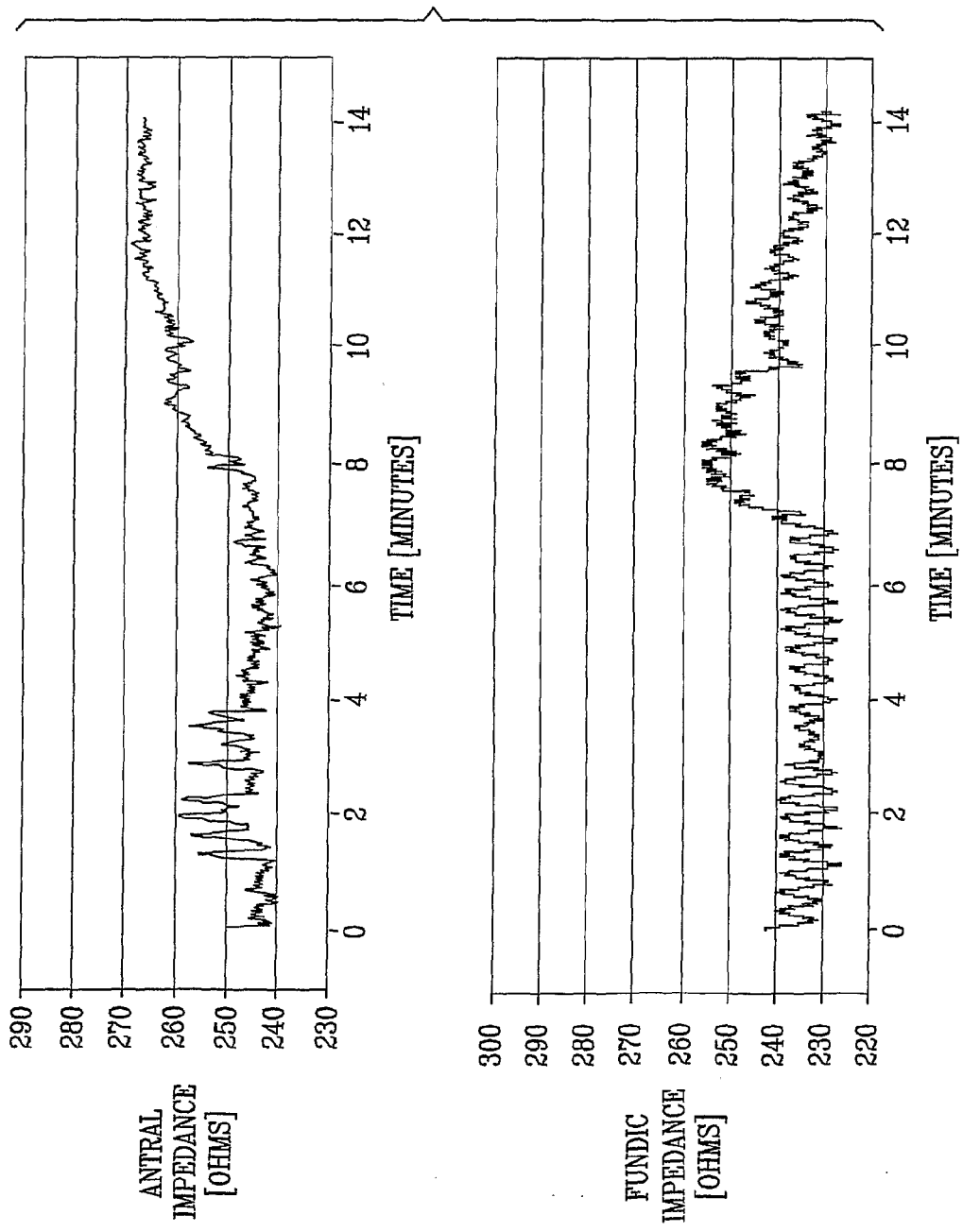

ANALYSIS AND REGULATION OF FOOD INTAKE

CROSS-REFERENCE TO RELATED APPLICATIONS

This application is a U.S. National Phase filing of copending, commonly assigned PCT Patent Application No. PCT/IL2008/000646, filed May 11, 2008, which is based upon and claims priority of commonly assigned U.S. Provisional Patent Application No. 60/916,919, filed May 9, 2007 and U.S. Provisional Patent Application No. 61/051,901, filed May 9, 2008, all of which are incorporated herein by reference in their entirety.

FIELD OF THE INVENTION

The present invention relates generally to tracking eating habits, and specifically to invasive techniques and apparatus for detecting and analyzing the ingestion and content of food.

BACKGROUND OF THE INVENTION

Obesity is a difficult to treat chronic condition defined by a body mass index (BMI=mass/height$^2$ [kg/m$^2$]) greater than 30. For obese persons, excessive weight is commonly associated with increased risk of cardiovascular disease, diabetes, degenerative arthritis, endocrine and pulmonary abnormalities, gallbladder disease and hypertension. Additionally, such persons are highly likely to experience psychological difficulties because of lifestyle restrictions such as reduced mobility and physical capacity, due to back pain, joint problems, and shortness of breath. In severe cases, this can contribute to absenteeism and unemployment. Moreover, impairment of body image can lead to significant psychological disturbances. Repeated failures of dieting and exercise to resolve the problem of obesity can result in feelings of despair and the development of clinical depression.

Bariatric surgery is often recommended for persons suffering from morbid obesity. Preferably, the invasive treatment is accompanied by changes in lifestyle, such as improved regulation of eating habits and an appropriate exercise regimen. Such lifestyle changes are dependent upon the self-discipline and cooperation of the patient.

A book entitled, *Textbook of Gastroenterology*, 3rd edition, edited by Yamada (Lippincott, Williams & Wilkins), which is incorporated herein by reference, has in Chapter 10 thereof a description of the physiology of gastric motility and gastric emptying.

An abstract entitled, "Gastric myoelectrical pacing as therapy for morbid obesity: Preliminary results," by Cigaina et al., retrieved on Dec. 24, 2000 from the Web-site http://www.med-online.com/transneuronix/Product/abstract.htm, which is incorporated herein by reference, describes a method for applying monopolar and bipolar gastric stimulation to achieve weight loss.

An abstract entitled, "Implantable gastric stimulator (IGS) as therapy for morbid obesity: Equipment, surgical technique and stimulation parameters," by Cigaina et al., retrieved on Dec. 24, 2000 from the Web-site http://www.med-online.com transneuronix/Product/abstract.htm, which is incorporated herein by reference, describes techniques of electrical signal therapy designed to treat obesity.

Stein et al., in an article entitled, "Carrots and sticks: Impact of an incentive/disincentive employee flexible credit benefit plan on health status and medical costs," American Journal of Health Promotion, May/June 1999, V5, I13, 5, which is incorporated herein by reference, describes providing incentives relating to medical care.

Giuffrida, in an article entitled, "Should we pay the patient? Review of financial incentives to enhance patient compliance," Biomedical Journal, vol. 315, pp. 703-707, 1997, which is incorporated herein by reference, describes providing incentives for enhanced patient compliance.

PCT Publication WO 06/018851 to Kliger et al., which is assigned to the assignee of the present application and is incorporated herein by reference, describes gastric apparatus including one or more sensors adapted to generate respective sensor signals responsive to activity of a gastrointestinal tract of a subject. A control unit is adapted to receive and analyze the sensor signals and to determine that an eating event has occurred, responsive to at least one of the sensor signals and a threshold. The control unit identifies an aspect of at least one of the sensor signals deriving from rhythmic activity of the gastrointestinal tract that is not indicative of current eating by the subject, and modifies the threshold responsive to the aspect of the signals that derives from activity that is not indicative of current eating.

U.S. Pat. No. 5,188,104 to Wernicke et al., which is incorporated herein by reference, describes a method for treating patients with compulsive eating disorders, including the steps of detecting a preselected event indicative of an imminent need for treatment of the specific eating disorder of interest, and responding to the detected occurrence of the preselected event by applying a predetermined stimulating signal to the patient's vagus nerve appropriate to alleviate the effect of the eating disorder of interest. For example, the preselected event may be a specified level of food ingestion by the patient within a set interval of time, or the commencement of a customary mealtime according to the patient's circadian cycle, or the passage of each of a sequence of preset intervals of time, or the patient's own recognition of the need for treatment by voluntarily initiating the application of the stimulating signal to the vagus nerve. In cases in which the disorder is compulsive eating to excess, the stimulating signal is predetermined to produce a sensation of satiety in the patient. The occurrence of the preselected event is detected by summing the number of swallows of food by the patient within the set interval of time. In cases where the disorder is compulsive refusal to eat (anorexia nervosa), the stimulating signal is predetermined to produce a sensation of hunger or to suppress satiety in the patient. In operation of a stimulus generator for controlling and treating compulsive overeating (including binge eating), a pulsed signal from a pulse generator is applied to excitation/sensing electrodes, and the amplitude of the signal on these electrodes is a function of the impedance between them, which varies according to whether the esophagus is empty or has food passing through it (and therefore, between the electrodes). The peak signal amplitude on the electrodes is detected and averaged by a peak detector over a predetermined interval of time. This may be calibrated to differentiate between different types of swallowing, such as of solids versus liquids and/or short swallows versus long swallows. The period of time in question may be selected according to the individual patient's eating habits.

U.S. Pat. No. 6,571,127 to Ben-Haim et al., which is assigned to the assignee of the present patent application and are incorporated herein by reference, describes apparatus and methods for applying signals to smooth muscle so as to modify the behavior thereof. In particular, apparatus for controlling the stomach is described in which a controller applies an electrical field to electrodes on the stomach wall so as to modify the reaction of muscle tissue therein to an activation signal, while not generating a propagating action potential in the tissue. In the context of the present patent application and in the claims, the use of such a non-excitatory signal to modify the response of one or more cells to electrical activation thereof, without inducing action potentials in the cells, is referred to as Excitable-Tissue Control (ETC). Use of an ETC signal is described in the PCT Patent Publication with respect to treating obesity, by applying the ETC signal to the stomach so as to delay or prevent emptying of the stomach. In addition, a method is described for increasing the motility of the gastrointestinal tract, by applying an ETC signal to a portion of the tract in order to increase the contraction force generated in the portion.

PCT Patent Publication WO 02/082968 to Policker et al., which is assigned to the assignee of the present patent application and is incorporated herein by reference, describes apparatus and methods for detecting the occurrence of an eating event by a subject and analyzing the quantity and characteristics of the food ingested.

Gastric banding is the weight loss technique of choice for many surgeons. Among the commercially available gastric bands are LAPBAND (Bioenterics, Carpinteria, Calif.) and SAGB (Swedish Adjustable Gastric Band; Obtech Medical, 6310 Zug, Switzerland). In gastric banding, an inflatable silicone band is placed around the upper part of the stomach, thus forming a pouch that reduces the capacity of the stomach. Upon ingestion, food passes from the esophagus to the pouch, filling it relatively quickly. This is intended to achieve a sensation of fullness faster and to maintain it for a longer period. The diameter of the passage remaining below the pouch is adjustable (by tightening or loosening the band typically using saline injected or pumped out from the band cavity), so that the band inflation will match individual parameters that are known to vary between patients and also vary in the same patient during the course of treatment. Solid intake is more sensitive to constriction than liquid intake; a restriction that reduces solid consumption significantly may have little effect on liquid consumption, whereas the tight restriction required to limit liquid consumption, might cause solid consumption to become difficult for the patient. Moreover, significant over-restriction may result in higher rates of band complications. Surgeons therefore try to find the "sweet spot" of restriction that gives the best trade-off between the need to have side-effect free solid intake but still good restriction of liquids.

PCT Publication WO 04/112563 to Ben Haim et al., which is assigned to the assignee of the present application and is incorporated herein by reference, describes inter alia an apparatus for detecting eating by a subject, comprising two electrodes, adapted for coupling to respective sites on a stomach of the subject; and a control unit, adapted to: drive a current between the electrodes, measure, responsive to the current, an electrical impedance between the sites, generate an impedance signal responsive to the measured electrical impedance, detect a change in posture of the subject by performing a posture analysis of the impedance signal, detect an indication of potential eating by the subject by performing an eating analysis of the impedance signal, and responsive to the posture analysis, interpret the impedance signal as indicative of the eating. In some embodiments, the control unit is adapted to adjust a volume of the stomach responsively to the indication of eating, optionally by tightening a controllable mechanical and/or electrical gastric device (e.g., a gastric band) around the stomach.

U.S. Pat. No. 5,868,141 to Ellias, which is incorporated herein by reference, describes an endoscopic stomach insert for reducing a patient's desire to eat.

U.S. Pat. No. 6,067,991 to Forsell, U.S. Pat. No. 5,601,604 to Vincent, U.S. Pat. No. 5,234,454 to Bangs, U.S. Pat. No. 4,133,315 to Berman et al., U.S. Pat. No. 4,416,267 to Garren et al., and U.S. Pat. Nos. 4,592,339, 5,449,368, 5,226,429 and 5,074,868 to Kuzmak, which are incorporated herein by reference, describe mechanical instruments for implantation in or around the stomach of an obese patient.

US Patent Application Publication 2003/0208212 to Cigaina, which is incorporated herein by reference, describes a removable gastric band for use in controlling obesity by allowing control and/or modification of the diameter of a patient's stomach. An electrostimulator may be incorporated into the design of the gastric band such that it would be in contact with the stomach when the gastric band is properly positioned, or implanted separately from the device.

US Patent Application Publication 2008/0097188 to Pool et al., which is incorporated herein by reference, describes techniques for quantifying the amount or rate of magnetically susceptible fluid within a gastric lumen. In one aspect, a magnetic sensor located external to the patient is configured to detect a quantity of fluid disposed within the gastric lumen. The quantity of fluid may include fluid that is contained upstream with respect to a restriction formed in the gastric lumen (e.g., by a gastric restriction device). The quantity of fluid disposed within the gastric lumen is determined by the magnetic sensor. This quantity may be evaluated over time to then calculate a real time flow rate which can then be displayed to the physician. The methods and devices allow a physician or other trained person to dynamically view real time development of fluid flow within a restricted gastric lumen and may be used in conjunction with adjustments to the gastric restriction device to achieve target or desired flow rates. In an embodiment, the gastric restriction device generally includes an adjustable band that at least partially or fully wraps around a portion of the patient's stomach or esophagus and is connected to an implantable interface that is located subcutaneously (or elsewhere) inside the patient.

PCT Publication WO 06/118790 to Maschino et al., which is incorporated herein by reference, describes techniques for treating an eating disorder with a gastric band and vagus nerve stimulation sufficient to induce afferent and/or efferent action potentials on the vagus nerve. The system comprises an implantable gastric band contacting the patient's gastrointestinal tract, and a pulse generator coupled to electrodes on the inner surface of the band for providing an electrical signal sufficient to induce afferent action potentials on the patient's vagus nerve. The gastric band preferably includes both sensing and stimulation electrodes, with the sensing electrodes being used for detecting induced afferent action potentials on the nerve and to identify which stimulation electrodes are nearest to the vagus nerve.

US Patent Application Publication 2006/0173238 to Warren, which is incorporated herein by reference, describes a dynamically controlled gastric occlusion device that monitors at least one physiological parameter that varies as a function of food intake and controls the degree of gastric constriction of an occluding device, such as a gastric band, based on the monitored physiological parameter.

US Patent Application Publication 2004/0167583 to Knudson et al., which is incorporated herein by reference, describes a method for treating at least one of a plurality of disorders of a patient characterized at least in part by vagal activity innervating at least one of a plurality of organs of the patient, including positioning a neurostimulator carrier around a body organ of the patient where the organ is innervated by at least a vagal trunk. An electrode is disposed on the carrier and positioned at the vagal trunk. An electrical signal is applied to the electrode to modulate vagal activity by an amount selected to treat the disorder. The signal may be a blocking or a stimulation signal. In an embodiment, electrodes are placed on constricting bands (such as the Lap-Band® system manufactured by Inamed Inc. (Santa Barbara, Calif., USA)), and used in obesity treatment. More preferably, the bands are not constricting thereby minimizing erosion risks otherwise associated with highly constricting bands. However, the neural blocking technology can be incorporated into such constricting bands or used in conjunction other obesity surgeries or therapies.

US Patent Application Publication 2005/0222638 to Foley et al., which is incorporated herein by reference, describes a method for treatment of obesity and other syndromes related to motor disorders of the stomach. The disclosed method utilizes a sensor to detect food entering the patient's stomach, thereby the sensor communicates with and activates at least one electrical stimulation device attached to either the stomach or the small intestine. One such sensor could be an elastic band around a portion of the stomach (e.g., passing around the stomach in the area of the lesser and greater curvatures).

U.S. Pat. No. 4,592,339 to Kuzmak et al., which is incorporated herein by reference, describes a gastric band for forming a stoma opening in a stomach for treating morbid obesity. The band is invasively placed around the stomach, and an expandable portion of the band is used to adjust the diameter of the stoma opening.

U.S. Pat. Nos. 5,449,368, 5,226,429, and 5,074,868 to Kuzmak, which are incorporated herein by reference, describe adjustable gastric bands. The size of the stoma opening of the bands can be adjusted by injecting into or removing fluid from an expandable section of the gastric bands.

U.S. Pat. No. 5,601,604 to Vincent, which is incorporated herein by reference, describes a gastric band for placement around the stomach for treating morbid obesity. The inner surface of the band is inflatable through a remote fill port. The band is invasively placed in an encircling position around the stomach by the facile closure of a single fastening means. After the band is fastened around the stomach, a fluid is injected into the inflatable inner surface, thereby constricting the stoma of the stomach.

U.S. Pat. No. 5,658,298 to Vincent et al., which is incorporated herein by reference, describes a tool for tightening a band or ligature having a buckle end and a free end during laparoscopic surgery.

PCT Publication WO 01/83019 to Vincent, which is incorporated herein by reference, describes apparatus and methods for transferring particles and fluids to or from a body of a patient, including inflating a balloon inside the body during surgical procedures to facilitate the identification of anatomical landmarks and to provide guidance for surgical dissections.

U.S. Pat. No. 5,938,669 to Klaiber et al., which is incorporated herein by reference, describes an adjustable gastric band for contracting a patient's stomach in order to fight obesity. A gastric band of a known type, implanted around the stomach and including a cavity filled with liquid, is connected by a tube to a control box and a balancing reservoir which are implanted under the skin of the patient. The box contains an electric pump and an electronic control unit capable of communicating by radio with a monitor carried by the patient and with a controller intended for the doctor. The controller can operate the pump by remote control to transfer determined volumes of liquid in a closed circuit from the gastric band to the reservoir or vice versa, to adjust the diameter of a passage in the stomach. The monitor receives and signals alarms from the control box.

U.S. Pat. No. 6,067,991 to Forsell, which is incorporated herein by reference, describes an adjustable gastric band including an elongated non-inflatable restriction member, a forming device for forming the restriction member into at least a substantially closed loop around the stomach or the esophagus to define a restriction opening, and a post-operation non-invasive adjustment device for mechanically adjusting the restriction member in the loop to change the size of the restriction opening.

U.S. Pat. No. 6,210,347 to Forsell, which is incorporated herein by reference, describes a food intake restriction device for forming a stoma opening in the stomach or esophagus of a patient. The device comprises an elongated restriction member to be formed into at least a substantially closed loop defining a restriction opening, and a controllable adjustment device for adjusting the restriction member in the loop to change the size of the restriction opening. The device further comprises a wireless remote control for controlling the adjustment device from outside the body of the patient in a non-invasive manner to assist in treating the patient for morbid obesity.

U.S. Pat. No. 6,460,543 to Forsell, which is incorporated herein by reference, describes a food intake restriction device for forming a stoma opening in the stomach or esophagus of a patient. The device comprises an elongated restriction member forming an expandable and contractible cavity formed into an at least substantially closed loop defining a restriction opening, the size of which is reduced upon expansion of the cavity and increased upon contraction of the cavity. A reservoir containing a predetermined amount of hydraulic fluid and connected to the cavity of the restriction member, and a hydraulic operation device for distributing fluid from the reservoir to the cavity to expand the cavity and for distributing fluid from the cavity to the reservoir to contract the cavity, are also implanted in a patient with morbid obesity and operated from outside the body of the patient in a non-invasive manner. A non-inflatable restriction member may alternatively be used, and hydraulically adjusted.

U.S. Pat. No. 6,453,907 to Forsell, which is incorporated herein by reference, describes an adjustable gastric band that includes an energy transmission device for wireless transmission of energy of a first form from outside the body of the patient. The band is adjusted in response to a second energy form different than the first form to vary the restricted stoma. An energy transfer device is implanted in the patient for transferring energy of the first form transmitted by the energy transmission device into energy of the second form.

U.S. Pat. No. 6,454,699 to Forsell, which is incorporated herein by reference, describes food intake restriction apparatus that includes a restriction device implanted in a patient, which engages the stomach or esophagus to form an upper pouch and a restricted stoma opening in the stomach or esophagus. The apparatus includes a source of energy external to the body of the patient, and a control device for releasing wireless energy from the source of energy from outside the body. The released wireless energy is used in connection with the operation of the restriction device, to enlarge it to allow food passage, or to contract it to substantially prevent food passage. The restriction device optionally includes at least one implanted sensor for sensing at least one physical parameter of the patient, in which case the control device may control the restriction device in response to signals from the sensor.

US Patent Application Publication 2003/0066536 to Forsell, which is incorporated herein by reference, describes food intake restriction apparatus, including an operable restriction device implanted in a patient and engaging the stomach or esophagus to form a restricted stoma opening in the stomach or esophagus. The apparatus includes a source of energy for energizing the restriction device, and a control device for releasing energy from the source of energy from outside the body of the patient. The released energy is used in connection with the operation of the restriction device to vary the size of the stoma opening to allow or substantially prevent the passage of food therethrough. The restriction apparatus optionally includes a pressure sensor for directly or indirectly sensing the pressure in the stomach. The control device may control the restriction device in response to signals from the pressure sensor.

US Patent Application Publication 2001/0011543 to Forsell, which is incorporated herein by reference, describes apparatus for treating morbid obesity or heartburn and reflux disease, including an elongated restriction member formed in a substantially closed loop around a stomach or esophagus of a human to form a stoma opening in the stomach or esophagus. The size of the stoma opening is adjustable by an implanted adjustment device. A control device is utilized to control the adjustment device, in order to either reduce or enlarge the size of the stoma opening, for example in response to the time of the day. A sensor, such as a pressure or position sensor, is surgically implanted in the body of the human so that the sensor may either directly or indirectly sense a physical parameter of the human, such as the pressure in the stomach or the human's orientation with respect to the horizontal. If in response to sensing by the sensor it is determined by the control device that a significant change in the physical parameter has occurred, then the control device controls the adjustment device to either reduce or enlarge the size of the stoma opening.

PCT Publication WO 01/41671 to Cigaina, which is incorporated herein by reference, describes a removable gastric band for controlling obesity by allowing control and/or modification of the diameter of a stomach of a patient. The gastric band comprises a closure mechanism, which allows the elongated body to close around a portion of the stomach. The gastric band can be used in conjunction with a gastric electrostimulator, and is therefore described as being potentially useful for inducing forced slimming in the initial phase of treatment for morbigenous obesity. Such electrostimulation devices may either be incorporated into the removable gastric band or located at a distance from the removable gastric band.

European Patent Application Publication 1 036 545 A2 to Moshe, which is incorporated herein by reference, describes a gastric band for attaching around a circumference of a stomach of a patient, so as to define the diameter of the stomach opening. The band comprises outer and inner surfaces, wherein the inner surface engages the stomach, and at least the outer surface is formed by an elongated member substantially non-extendable along a longitudinal axis thereof. A through-going opening is made in the elongated member and is located so as to define an end portion of the band having a predetermined length. An opposite end portion of the band is shaped so as to be insertable into the through-going opening, for adjusting a desired inner diameter of the band in its closed operating position and fastening the opposite end portion to the outer surface of the band.

U.S. Pat. No. 6,511,490 to Robert, which is incorporated herein by reference, describes a gastric banding device for implantation within a person for the treatment of morbid obesity. The gastric banding device includes an inflatable band portion dimensioned to encircle the stomach, and an inflation conduit operable for conducting a percutaneously injected inflation fluid into the band portion. The band portion is a toroidal member having a head end with first fastening means thereon and a tail end having second fastening means thereon and an inflatable shell therebetween. The outer surface of the toroidal shell in reinforced with a non-extensible, biocompatible material which serves to limit outward expansion of the shell when an inflation fluid is injected thereinto. The inner, stomach-contacting surface of the shell has a layer of an open-cell elastomeric foam affixed thereto and integral therewith. In operation, when the band is placed in an encircling relationship with the stomach, the first and second fastening means on the ends of the shell are engaged in locking relationship. An inflation fluid is injected into the shell by means of a subcutaneously implanted injection port that is in fluid communication with the inflation conduit. As the shell expands inwardly, it constricts and compartmentalizes the stomach.

U.S. Pat. No. 6,547,801 to Dargent et al., which is incorporated herein by reference, describes an implantable gastric constriction device comprising a constriction member forming a ring in its operational configuration. The constriction member includes a flexible band, of which the two ends are adjacent to one another in the operational configuration, and a means for actuating the constriction member, characterized in that, in cooperation, on the one hand, at least one end of the flexible band includes a tractile element for moving such end relative to the other end, generating a radial deformation of the constriction member, and, on the other hand, the actuating means comprises a member for pulling the tractile element.

The following patents and patent application publications, all of which are incorporated herein by reference, may be of interest:

U.S. Pat. No. 6,270,455 to Brown
U.S. Pat. No. 6,129,685 to Howard
U.S. Pat. No. 4,823,808 to Clegg et al.
U.S. Pat. No. 5,690,691 to Chen et al.
U.S. Pat. No. 5,423,872 to Cigaina
U.S. Pat. No. 5,263,480 to Wernicke et al.
U.S. Pat. Nos. 6,104,955, 6,091,992, 5,995,872, and 5,836,994 to Bourgeois
U.S. Pat. No. 6,026,326 to Bardy
U.S. Pat. No. 3,411,507 to Wingrove
U.S. Pat. No. 5,979,449 to Steer
U.S. Pat. No. 4,975,682 to Kerr et al.
U.S. Pat. No. 5,861,014 to Familoni
U.S. Pat. No. 5,716,385 to Mittal et al.
U.S. Pat. No. 6,415,178 to Ben-Haim et al.
US Patent Application Publication 2004/0098068 to Carbunaru et al.
U.S. Pat. No. 6,516,227 to Meadows et al.
US Patent Application Publication 2003/0114899 to Woods et al.
U.S. Pat. No. 6,185,452 to Schulman et al.
US Patent Application Publication 2004/0106963 to Tsukamoto et al.

SUMMARY OF THE INVENTION

In some embodiments of the present invention, apparatus for detecting the ingestion and content of liquid and solid food comprises fundic and antral sensors coupled to a fundic region and an antral region of a stomach of a subject, respectively. A control unit determines whether the ingested food is predominantly solid or liquid and/or includes at least a given amount of liquids regardless of the amount of solids ingested, by analyzing fundic and/or antral impedances measured by the sensors. For some applications, the control unit interprets a change in antral impedance vs. baseline of less than a threshold value as indicating that the ingested food is predominantly solid. Alternatively or additionally, the control unit calculates a duration of the period during which fundic impedance rises from baseline during ingestion of the food. The control unit interprets a duration greater than a threshold value as indicating that the ingested food is predominantly solid. For some applications, the control unit alternatively or additionally analyzes an antral local sense rate detected by the antral sensor. The control unit interprets a substantial reduction in the rate over a brief period of time, after which the rate returns to baseline, as indicating that the ingested food is predominantly liquid.

In some embodiments of the present invention, the control unit detects ingestion of predominantly solid food by the subject using an ingestion detection algorithm that is adapted to minimize two types of false positive detections: (a) a false positive detection of ingestion, i.e., the subject has not ingested any solid or liquid food, and (b) a false positive detection of ingestion of predominantly solid food, i.e., the subject has ingested food, but the food is predominantly liquid rather than predominantly solid. The algorithm typically makes a tentative determination of ingestion of predominantly solid food upon detecting that (a) an increase in fundic impedance vs. a baseline (measured during pre-intake period) level is greater than a first threshold value, and/or (b) an antral local sense rate is less than a second threshold value, typically as measured over a number of events (an "event" being detected by, for example, detecting an electric complex by threshold crossing, measured using one or more electrodes, where the complex is indicative of a propagating action potential in the antrum), e.g., about six events. The algorithm determines that the tentative determination of ingestion of predominantly solid food is a false positive if either of the following conditions is met: (a) no ingestion has occurred, as indicated by a duration of the period during which the fundic impedance rose during tentative ingestion being less than a threshold value, or (b) the ingested food is predominantly liquid.

For some applications, the algorithm determines that the ingested food is predominantly liquid if at least a certain number of the following conditions are met, such as at least one, two, three, or all of the conditions, or a combination of certain ones of the conditions: (i) fundic impedance change is greater than a threshold value, (ii) a duration of the period during which the fundic impedance rose during tentative ingestion is less than a threshold value, (iii) antral impedance change is greater than a threshold value immediately following the change in fundic impedance, and/or (iv) a substantial reduction in an antral local sense rate is observed over a brief period of time, after which the rate returns to baseline.

The threshold values indicating ingestion and false positives are typically adjustable to ensure accurate detection of ingestion by the subject. For some applications, the threshold values indicative of ingestion are modified through the use of a control unit that adapts the threshold values by checking that an indicated ingestion event corresponds to an actual detection event. Such checking may include relying on (a) the subject or another person (e.g., a healthcare worker) to verify or deny an ingestion event, either periodically, occasionally, and/or during a calibration period, and/or (b) additional sensor information. For example, a repeated false positive indication of ingestion due to normal gastric activity would cause one or more of the threshold values used to signify an ingestion event to be modified.

In some embodiments of the present invention, the apparatus comprises a gastric band, configured to mechanically modify a volume of a stomach of a patient. The gastric band is configured to be placed around the stomach and to be tightened so as to cause a narrowing of the stomach, thereby reducing the volume of the stomach.

For some applications, a specific schedule of allowed food ingestion is pre-programmed by the physician into the memory, and a processor is continuously operative to detect whether food ingestion is taking place in accordance with the programmed schedule. For some subjects, the schedule may be less strict with respect to drinking certain types of liquids, and more strict with respect to ingestion certain types of solid food. When an exception from the schedule is detected, the processor typically actuates a signal generator to generate a signal that discourages the subject from continued ingestion. For example, the signal may include an ingestion-control signal, a satiety inducing signal, a visual, audio, or other cue, or a discomfort-inducing signal. For example, techniques may be used that are described in one or more of the following patent applications, all of which are assigned to the assignee of the present application and are incorporated herein by reference:

U.S. Provisional Patent Application 60/259,925, filed Jan. 5, 2001, entitled, "Regulation of eating habits";

PCT Patent Application PCT/IL02/00007, filed Jan. 3, 2002, entitled, "Regulation of eating habits";

PCT Patent Application PCT/IL04/000664, filed Jul. 21, 2004, entitled, "Gastrointestinal methods and apparatus for use in treating disorders and controlling blood sugar";

U.S. patent application Ser. No. 09/734,358, filed Dec. 21, 2000, entitled, "Acute and chronic electrical signal therapy for obesity," which issued as U.S. Pat. No. 6,600, 953; and/or PCT Patent Application PCT/IL05/000904, filed Aug. 18, 2005, entitled, "Monitoring, analysis, and regulation of eating habits."

For some applications, impedance and other electrical activity response criteria of the stomach of an individual subject are determined and calibrated by measuring the response of the subject's stomach to various types of solid and liquid food. To ensure appropriate compliance, calibration is typically performed under the supervision of a healthcare worker.

In some embodiments, the collected data are stored and intermittently uploaded to an external computer, typically by a wireless communications link, for review by the subject's physician, to enable monitoring of the subject's adherence to a dietary regimen.

"Food," as used in the present application including the claims, is to be understood as including both solid and liquid food, unless otherwise indicated.

In some embodiments of the present invention, the gastric device comprises a gastric band, configured to be placed around the stomach, and to be tightened and loosened in real time, responsive to signals received from the control unit. Tightening of the band causes a narrowing of the stomach, thereby reducing the volume of the stomach.

In an embodiment, the method includes tightening a gastric band around the stomach, thereby reducing a volume of the stomach, responsively to the indication of ingestion of solid food but not responsively to the indication of ingestion of a liquid. Alternatively or additionally, reducing the volume of the stomach responsively to the indication of ingestion of solid food but not responsively to the indication of ingestion of a liquid includes applying an electrical signal to the stomach, and configuring the electrical signal to modify a contraction pattern of one or more muscles of the stomach.

There is therefore provided, in accordance with an embodiment of the present invention, apparatus including:

one or more fundic sensors, configured to be applied to a fundus of a subject, and to generate a fundic signal; and
a control unit, configured to:
make a tentative determination of ingestion by the subject,
determine fundic impedance responsively to the fundic signal,
calculate a duration of a period during which the fundic impedance rose during the tentatively-determined ingestion, and
determine that the tentative determination of ingestion is a false positive upon finding that the duration is less than a fundic rise duration threshold value.

For some applications, the control unit is configured to make the tentative determination of ingestion by interpreting an increase in fundic impedance vs. a baseline level greater than a fundic increase threshold value as tentatively indicative of the ingestion.

For some applications, the apparatus includes one or more antral sensors, configured to be applied to an antrum of the subject, and to generate an antral signal, and the control unit is configured to make the tentative determination of ingestion by determining an antral local sense rate responsively to the antral signal, and finding that the antral local sense rate is less than a local sense rate threshold value.

For some applications, the apparatus includes one or more antral sensors, configured to be applied to an antrum of the subject, and to generate an antral signal, and the control unit is configured to make the tentative determination of ingestion by determining an amplitude of antral contractions responsively to the antral signal, and finding that the antral contractions amplitude is greater than an antral contractions amplitude threshold value.

For some applications, the apparatus includes one or more antral sensors, configured to be applied to an antrum of the subject, and to generate an antral signal, and the control unit is configured to make the tentative determination of ingestion by determining an antral local sense rate responsively to the antral signal, determining an amplitude of antral contractions responsively to the antral signal, and analyzing a combination of: (a) a comparison of the antral local sense rate with a local sense rate threshold value, and (b) a comparison of the antral contractions amplitude and an antral contractions amplitude threshold value.

In an embodiment, the control unit is configured to make a solid/liquid determination of whether the ingested food is predominantly solid or predominantly liquid. For some applications, the apparatus includes a gastric band, and the control unit is configured to cause tightening of the gastric band responsively to the solid/liquid determination. For some applications; the apparatus includes one or more antral sensors, configured to be applied to an antrum of the subject, and to generate an antral signal, and the control unit is configured to make the solid/liquid determination by determining antral impedance responsively to the antral signal, calculating a correlation between changes in the antral impedance and changes in the fundic impedance over a period of time having a duration of between one and 10 minutes, and determining that the food is predominantly liquid upon finding that the correlation is greater than a threshold correlation value.

There is further provided, in accordance with an embodiment of the present invention, apparatus including:
one or more antral sensors, configured to be applied to an antrum of the subject, and to generate an antral signal; and
a control unit, configured to:
detect ingestion of food by the subject,
determine antral impedance responsively to the antral signal, and
interpret a change in antral impedance vs. a baseline value of less than a threshold value as indicating that the ingested food is predominantly solid.

There is still further provided, in accordance with an embodiment of the present invention, apparatus including:
one or more fundic sensors, configured to be applied to a fundus of the subject, and to generate a fundic signal; and
a control unit, configured to:
detect ingestion of food by the subject,
determine fundic impedance responsively to the fundic signal,
calculate a duration of a period during which the fundic impedance rose during the ingestion, and
determine that the ingested food is predominantly solid upon finding that the duration of the period is greater than a threshold value.

For some applications, the threshold value is between one and five minutes. For some applications, the threshold value includes a first threshold value, and the control unit is configured to determine that the ingested food is predominantly liquid upon finding that the duration of the period is less than a second threshold value. For example, the second threshold value may be between 10 seconds and five minutes.

There is additionally provided, in accordance with an embodiment of the present invention, apparatus including:
one or more antral sensors, configured to be applied to an antrum of the subject, and to generate an antral signal; and
a control unit, configured to:
detect ingestion of food by the subject,
calculate an antral local sense rate responsively to the antral signal, and
determine that the ingested food is predominantly liquid upon finding that a reduction in the rate over a period of time is greater than a first threshold value, the period of time commencing during the ingestion of the food and having a period duration of less than a second threshold value.

For some applications, the period duration equals the duration of between one and three detected antral waves. For some applications, the control unit is configured to receive an antral local sense baseline rate, and to set the first threshold value to be between 25% and 75% of the baseline rate. For some applications, the control unit is configured to receive an antral local sense baseline rate, and to determine that the ingested food is predominantly liquid only upon finding that the reduction in the rate over the period of time is greater than the first threshold value, and that the rate returns to the baseline rate after a conclusion of the period of time.

There is still additionally provided, in accordance with an embodiment of the present invention, apparatus including:
one or more fundic sensors, configured to be applied to a fundus of a subject, and to generate a fundic signal; and
a control unit, configured to:
make a determination of ingestion of food by the subject,
determine fundic impedance responsively to the fundic signal,
calculate a maximum rise rate, expressible as a measure of resistance over a measure of time, in the fundic impedance during at least one period of the ingestion, and
determine that the ingested food is liquid upon finding that the rise is at least equal to a fundic rise threshold value.

For some applications, the fundic rise threshold value is between one and 30 ohms per second.

There is also provided, in accordance with an embodiment of the present invention, apparatus including:
a gastric band;

one or more gastrointestinal sensors, configured to be coupled to one or more gastrointestinal sites of a subject and to generate one or more gastrointestinal sensor signals responsive to a property of at least one of the gastrointestinal sites; and a control unit, configured to:
receive and analyze the one or more gastrointestinal sensor signals, and to determine, responsively thereto, an extent to which ingested food includes solid food matter, and
cause tightening of the gastric band in response to a determination that the ingested food includes predominantly the solid food matter.

For some applications, the one or more gastrointestinal sensors include one or more antral sensors, configured to be applied to an antrum of the subject, and to generate an antral signal, and the control unit is configured to detect ingestion of food by the subject, determine antral impedance responsively to the antral signal, and interpret a change in antral impedance vs. a baseline value of less than a threshold value as indicating that the ingested food includes predominantly the solid food matter.

For some applications, the one or more gastrointestinal sensors include one or more fundic sensors, configured to be applied to a fundus of the subject, and to generate a fundic signal, and the control unit is configured to detect ingestion of food by the subject, determine fundic impedance responsively to the fundic signal, calculate a duration of a period during which the fundic impedance rose during the ingestion, and determine that the ingested food includes predominantly the solid food matter upon finding that the duration of the period is greater than a threshold value.

For some applications, the one or more gastrointestinal sensors include one or more antral sensors, configured to be applied to an antrum of the subject, and to generate an antral signal, and the control unit is configured to detect ingestion of food by the subject, calculate an antral local sense rate responsively to the antral signal, determine that the ingested food is predominantly liquid upon finding that a reduction in the rate over a period of time is greater than a first threshold value, the period of time commencing during the ingestion of the food and having a duration of less than a second threshold value, and cause loosening of the gastric band responsively to the determination that the ingested food is predominantly liquid.

For some applications, the one or more gastrointestinal sensors include one or more fundic sensors, configured to be applied to a fundus of a subject, and to generate a fundic signal, and the control unit is configured to make a determination of ingestion of food by the subject, determine fundic impedance responsively to the fundic signal, calculate a rise in the fundic impedance during at least one period of the ingestion, determine that the ingested food is liquid upon finding that the rise is at least equal to a fundic rise threshold value, and cause loosening of the gastric band responsively to the determination that the ingested food is liquid.

In an embodiment, the apparatus includes one or more current application electrodes configured to be coupled to a gastrointestinal tract of the subject, and the control unit is configured to drive a current to at least one of the one or more current application electrodes responsively to the extent to which the ingested food includes the solid food matter. For some applications, the control unit is configured to drive the current only in response to the determination that the ingested food includes predominantly the solid food matter. For some applications, the control unit is configured to begin driving the current before causing the tightening of the gastric band. For some applications, the control unit is configured to cause a first level of the tightening of the gastric band during a first period during which the control unit drives the current, and a second level of the tightening of the gastric band during a second period during which the control unit does not drive the current, the first level less than the second level. For some applications, the control unit is configured to cause a first level of the tightening of the gastric band during a first period during which the control unit drives the current, and a second level of the tightening of the gastric band during a second period during which the control unit does not drive the current, the first level greater than the second level. For some applications, the control unit is configured to drive the current only in response to a determination that the ingested food is predominantly liquid.

For some applications, the control unit is configured to cause the tightening of the gastric band at a timing configured to cause weight loss in the subject. Alternatively or additionally, the control unit is configured to cause the tightening of the gastric band at a timing configured to control blood sugar in the subject.

For some applications, the control unit is configured to cause the tightening of the gastric band after a delay after making the determination that the ingested food includes predominantly the solid food matter. For example, the delay may include between 10 minutes and 30 minutes.

There is further provided, in accordance with an embodiment of the present invention, apparatus including:
a handheld portable device, including a device wireless communication module, and configured to provide a food diary for a subject, for aiding in behavior modification related to food intake;
one or more gastrointestinal sensors, configured to be coupled to one or more gastrointestinal sites of the subject and to generate one or more gastrointestinal sensor signals responsive to a property of at least one of the gastrointestinal sites;
an implantable wireless device communication module; and
a control unit, coupled to the implantable wireless device communication module, and configured to:
receive and analyze the one or more gastrointestinal sensor signals, and to determine, responsively thereto, an extent to which ingested food includes solid food matter, and
drive the implantable wireless device communication module to wirelessly transmit, to the device wireless communication module, an indication of the extent to which the ingested food includes the solid food matter,
wherein the handheld portable device is configured to record the indication in the food diary.

For some applications, the behavior modification include weight loss, and the food diary is configured to aid in the weight loss.

For some applications, the one or more gastrointestinal sensors include one or more antral sensors, configured to be applied to an antrum of the subject, and to generate an antral signal, and the control unit is configured to detect ingestion of food by the subject, determine antral impedance responsively to the antral signal, and interpret a change in antral impedance vs. a baseline value of less than a threshold value as indicating that the ingested food includes predominantly the solid food matter.

For some applications, the one or more gastrointestinal sensors include one or more fundic sensors, configured to be applied to a fundus of the subject, and to generate a fundic signal, and the control unit is configured to detect ingestion of food by the subject, determine fundic impedance responsively to the fundic signal, calculate a duration of a period during which the fundic impedance rose during the ingestion, and determine that the ingested food includes predominantly the solid food matter upon finding that the duration of the period is greater than a threshold value.

For some applications, the one or more gastrointestinal sensors include one or more antral sensors, configured to be applied to an antrum of the subject, and to generate an antral signal, and the control unit is configured to detect ingestion of food by the subject, calculate an antral local sense rate responsively to the antral signal, and determine that the ingested food is predominantly liquid upon finding that a reduction in the rate over a period of time is greater than a first threshold value, the period of time commencing during the ingestion of the food and having a duration of less than a second threshold value.

For some applications, the one or more gastrointestinal sensors include one or more fundic sensors, configured to be applied to a fundus of a subject, and to generate a fundic signal, and the control unit is configured to make a determination of ingestion of food by the subject, determine fundic impedance responsively to the fundic signal, calculate a rise in the fundic impedance during at least one period of the ingestion, and determine that the ingested food is liquid upon finding that the rise is at least equal to a fundic rise threshold value.

In an embodiment, the apparatus includes one or more current application electrodes configured to be coupled to a gastrointestinal tract of the subject, and the control unit is configured to drive a current to at least one of the one or more current application electrodes responsively to the extent to which the ingested food includes the solid food matter. For some applications, the control unit is configured to drive the current only in response to the determination that the ingested food includes predominantly the solid food matter. For some applications, the control unit is configured to drive the current only in response to a determination that the ingested food is predominantly liquid.

There is still further provided, in accordance with an embodiment of the present invention, apparatus including:

a gastrointestinal (GI) tract attachment element, configured to be coupled to a portion of a GI tract of a subject such that the element surrounds less than 360 degrees of the GI tract, and applies a constrictive force to the GI tract portion that causes at least a 5% reduction in a cross-sectional area of the GI tract in a vicinity of the portion; and at least one electrode, coupled to the attachment element such that the electrode contacts the GI tract portion when the attachment element is coupled to the GI tract portion.

For some applications, the attachment element is configured to cause the reduction to be at least 10%.

For some applications, the attachment element is configured to be coupled to the GI tract such that the element surrounds less than 270 degrees of the GI tract.

For some applications, the attachment element includes a clip.

In an embodiment, the GI tract portion is a stomach of the subject, and the attachment element is configured to be coupled to the stomach.

The present invention will be more fully understood from the following detailed description of embodiments thereof, taken together with the drawings, in which:

BRIEF DESCRIPTION OF THE DRAWINGS

FIG. 3A is a flow chart illustrating an algorithm for detecting ingestion of solid food, in accordance with an embodiment of the present invention;

FIG. 3B is a flow chart illustrating an algorithm for differentiating between ingestion of solid and liquid food, in accordance with an embodiment of the present invention;

FIGS. 4A-C and 5A-B are graphs showing the results of experiments performed using apparatus similar to the apparatus of FIG. 1A, and analysis thereof, in accordance with an embodiment of present invention;

DETAILED DESCRIPTION OF EMBODIMENTS

Figure 1A:
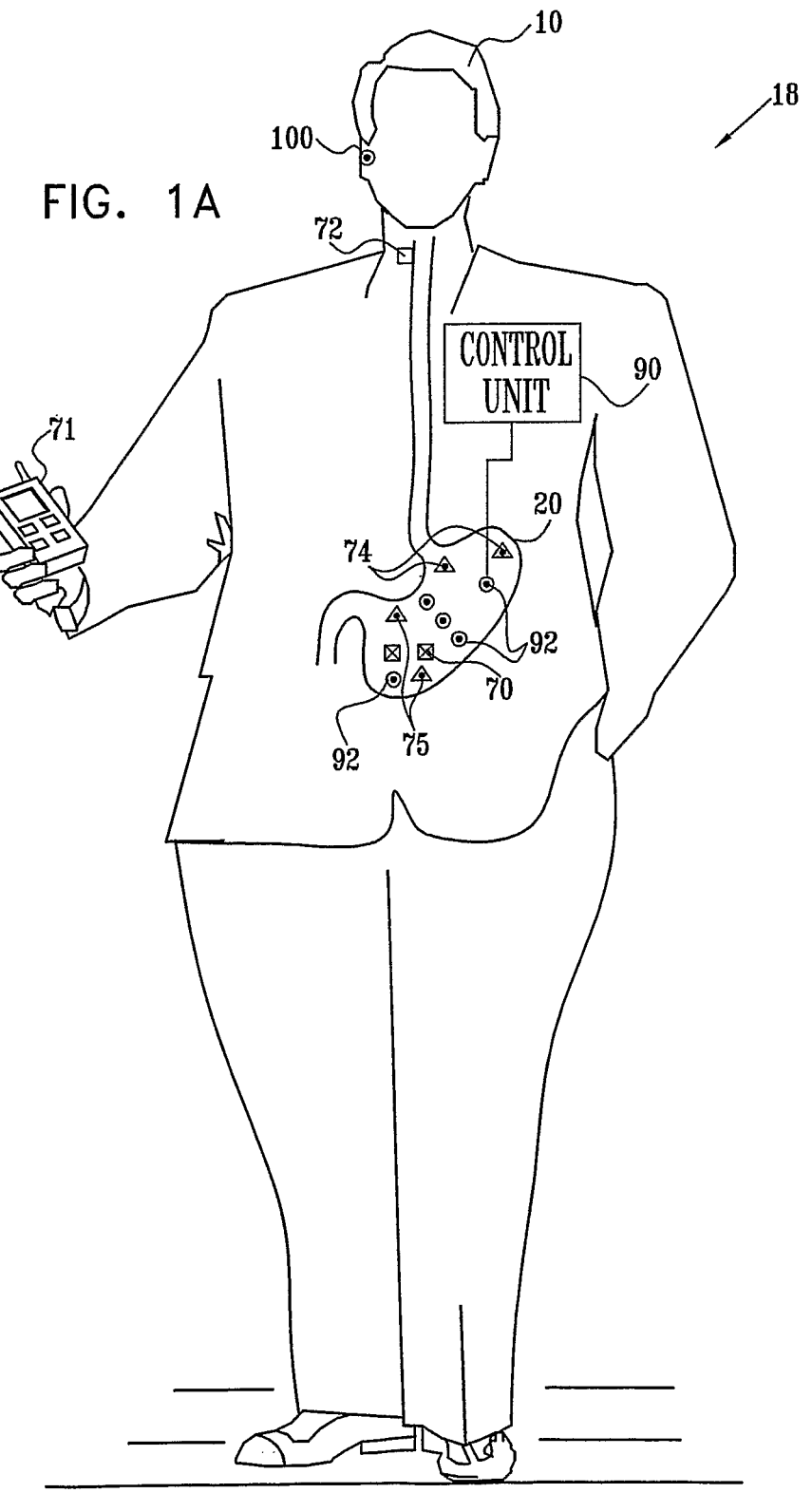
FIG. 1A is a schematic illustration of apparatus for detecting the ingestion and content of liquid and solid food, in accordance with an embodiment of the present invention.

FIG. 1A is a schematic illustration of apparatus 18 for detecting the ingestion and content of liquid and solid food, in accordance with an embodiment of the present invention. Apparatus 18 comprises fundic local sense electrodes 74, antral local sense electrodes 75, a control unit 90, and operator controls 71. For some applications, apparatus 18 further comprises one or more current-application electrodes 92, mechanical sensors 70, and/or supplemental sensors 72. In an embodiment, fundic local sense electrodes 74 are replaced or supplemented by other fundic change sensors, such as strain gauges, which similarly indicate distension of the fundus. Alternatively or additionally, antral local sense electrodes 75 are replaced or supplemented by other antral change sensors, such as strain gauges, which similarly indicate distension of the antrum.

Electrodes 74, 75, and 92 are typically coupled to the serosal layer of a stomach 20 of a subject 10 and/or inserted into the muscular layer of the stomach in the fundic and antral regions. For some applications, fundic local sense electrodes 74 are placed about 2.5 cm apart, approximately 2 cm inferior to the gastroesophageal junction, and antral local sense electrodes 75 are placed about 3 cm apart, approximately 3 cm above the pylorus. Alternatively or additionally, the electrodes are coupled elsewhere on the stomach, gastrointestinal tract, or to other suitable locations in or on the subject's body. The number of electrodes and sensors, as well as the positions thereof, are shown in FIG. 1A by way of example, and other sites on stomach 20 or in or on the subject's body are appropriate for electrode and sensor placement in other applications of the present invention. Different types of electrodes known in the art are typically selected based on the specific condition of the subject's disorder, and may comprise stitch, coil, screw, patch, basket, needle and/or wire electrodes, or substantially any other electrode known in the art of electrical stimulation or sensing in tissue.

Figure 1B:
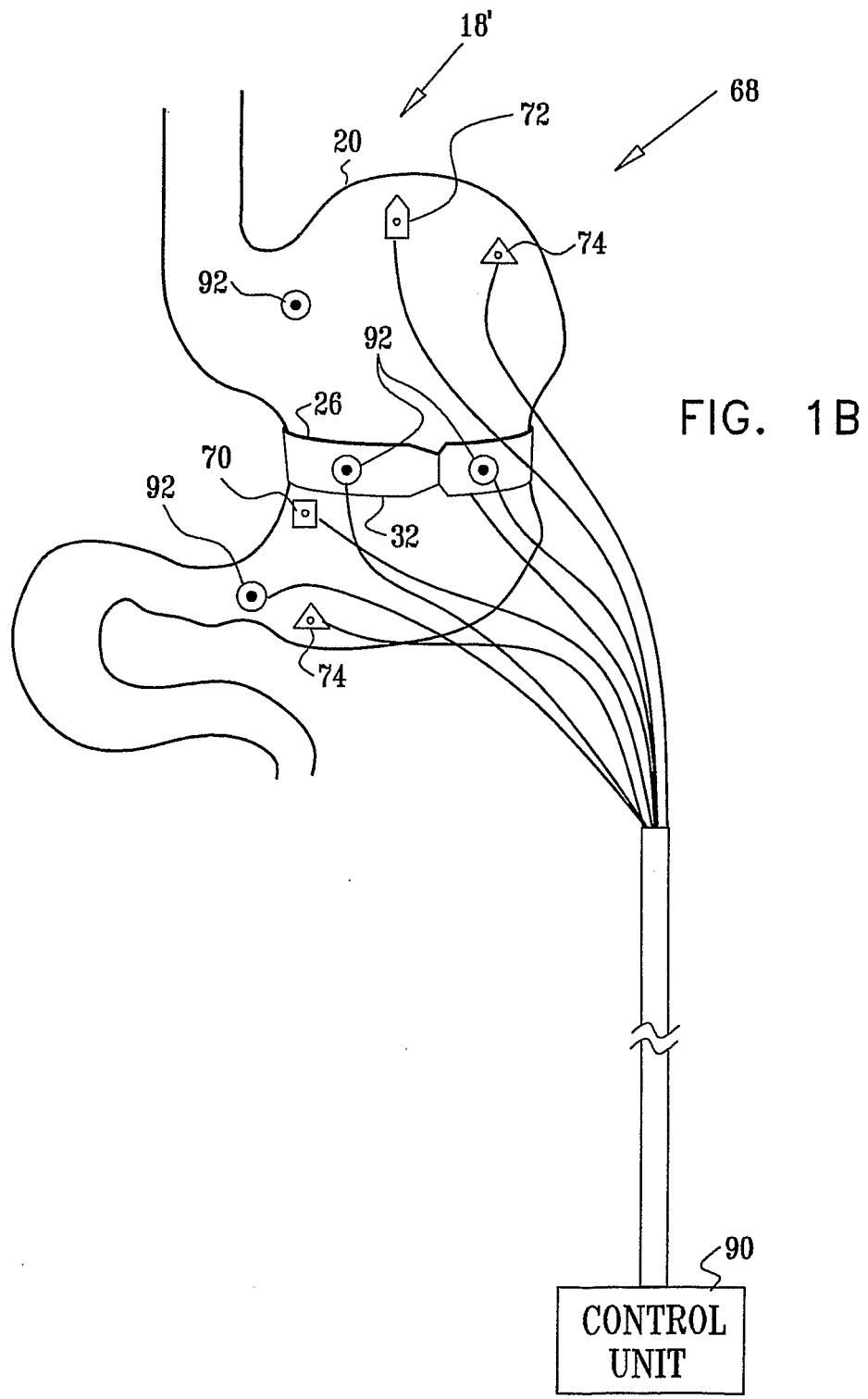
FIG. 1B is a schematic illustration of gastric control apparatus comprising an adjustable gastric band, in accordance with an embodiment of the present invention.

Reference is now made to FIG. 1B, which schematically illustrates gastric control apparatus 18', in accordance with an embodiment of the present invention. For the sake of simplicity, like elements to those described with respect to apparatus 18 shown in FIG. 1A are given the same reference numerals, and the following description details mainly the differences between apparatus 18 and apparatus 18'. Apparatus 18' comprises implantable or external control unit 90, and, as an alternative for or an addition to current application electrodes 92, a gastric band 32, configured to mechanically and/or electrically modify a volume of stomach 20. Gastric band 32 is configured to be placed around stomach 20 and to be tightened so as to cause a narrowing of stomach 20, thereby reducing the volume of the stomach. Like apparatus 18, apparatus 18' typically further comprises one or more sensors 70, 74, 75, and/or 72, as described hereinabove with reference to FIG. 1A. In an embodiment, one or more of the sensors (e.g., mechanical sensor 70) are fixed to an inner surface of gastric band 32.

Control unit 90 of apparatus 18' is configured to receive one or more signals from sensors 70, 74, 75, and/or 72, to analyze the signals, and, responsively to the analysis, to drive gastric band 32 to adjust in real-time the magnitude of stomach volume reduction. The reduced stomach volume increases the sensation of satiety felt by the subject compared to that which would be felt without such stomach volume reduction, and therefore generally reduces the subject's appetite so as to treat obesity of the subject. Such reduction is believed by the inventors to increase a sensation of satiety felt by the subject compared to that which was felt prior to tightening of the band. For some applications, control unit 90 drives current to one or more of application electrodes 92 to apply an electrical signal to the stomach responsively to the analysis. This signal may be delivered in addition to or instead of the driving of gastric band 32. Typically, the gastric band is configured such that the cross-sectional area of the stomach is reduced by at least 20%, and the control unit is configured to maintain this reduction in at least one region of the stomach for a period of at least one minute. It is to be understood that for some applications, greater or lesser reductions in cross-sectional area may be desirable, and these may be maintained for periods greater or less than one minute.

For some applications, active control of the size of gastric band 32 (particularly in combination with selective activation thereof in response to a determination of solid matter ingestion) reduces the frequency of follow-up visits to a doctor and/or the number of times that the level of band constriction is adjusted.

For some applications, apparatus 18 or 18' is implanted in subject 10 in a manner generally similar to that used to implant gastric pacemakers or other apparatus for stimulating or sensing in the gastrointestinal tract that are known in the art. As appropriate, techniques described in one or more of the references cited in the Background section of the present patent application may be adapted for use with these embodiments of the present invention. For some applications, electrode assemblies and/or techniques for implanting the electrodes are used which are described in International Patent Application PCT/IL2007/000052 to Levi et al., filed Jan. 14, 2007, entitled, "Electrode assemblies, tools, and methods for gastric wall implantation," which is assigned to the assignee of the present application and is incorporated herein by reference. Other methods and apparatus which may be useful in carrying out some embodiments of the present invention are described in the above-cited U.S. Provisional Patent Application 60/259,925, entitled, "Regulation of eating habits," filed on Jan. 5, 2001, and in the above-cited PCT patent application and in the above-cited U.S. Pat. No. 6,600,953, entitled, "Acute and chronic electrical signal therapy for obesity," filed on Dec. 11, 2000, which are assigned to the assignee of the present patent application and are incorporated herein by reference.

Reference is again made to FIG. 1B. As mentioned above, apparatus 18' may comprise one or more current application electrodes 92. Typically, control unit 90 drives current application electrodes 92 to apply an electrical signal to tissue of stomach 20, or another site of the GI.

For some applications, at least one of fundic local sense electrodes 74 is placed just proximal to gastric band 32 (i.e., on the wall that defines the pouch created by the band). In the case of a bipolar fundic lead, the other electrode 74 is typically implanted under the band (i.e., covered by the band, and optionally fixed to the band) or just distal to the band. In the case of a unipolar fundic lead, the single electrode 74 is typically placed proximal to the band. Alternatively, fundic local sense electrodes 74 are coupled to other sites of the fundus.

The circumference of gastric band 32 is bidirectionally adjustable in real time responsive to input from control unit 90. The gastric band typically, but not necessarily, utilizes one or more of the following techniques for controllably adjusting the circumference thereof:

Gastric band 32 comprises a motor, such as a linear motor or a rotary motor, which is configured to contract and expand gastric band 32. For example, motorized adjustment techniques may be used that are described in above-referenced U.S. Pat. Nos. 6,067,991 and/or 6,454,699, and/or in above-referenced US Patent Application Publications 2003/0066536 and/or 2001/0011543.

At least a portion of gastric band 32 comprises a temperature-sensitive material, the compliance and/or length of which varies in response to temperature changes. Control unit 90 applies changes in temperature to the material so as to achieve a desired stomach volume.

Gastric band 32 comprises a portion that is inflatable through a fill port. For example, an inner surface of the band may comprise the inflatable portion. Typically, the portion is inflated with a liquid, such as saline solution. The inflatable portion is typically connected by a tube to a balancing reservoir that is implanted under the skin of the subject. Band 32 further comprises a pump, which, responsive to input from control unit 90, transfers determined volumes of liquid in a closed circuit from the band to the reservoir or vice versa, to adjust the circumference of the band.

Adjustable band inflation techniques are used that are described in above-referenced U.S. Pat. Nos. 5,938,669, 6,460,543, 6,453,907, and/or 6,454,699, and/or in above-referenced US Patent Application Publication 2001/0011543.

Other techniques described in one or more of the publications referred to in the Background of the Invention are utilized for controllably adjusting the circumference of gastric band 32.

Figure 2:
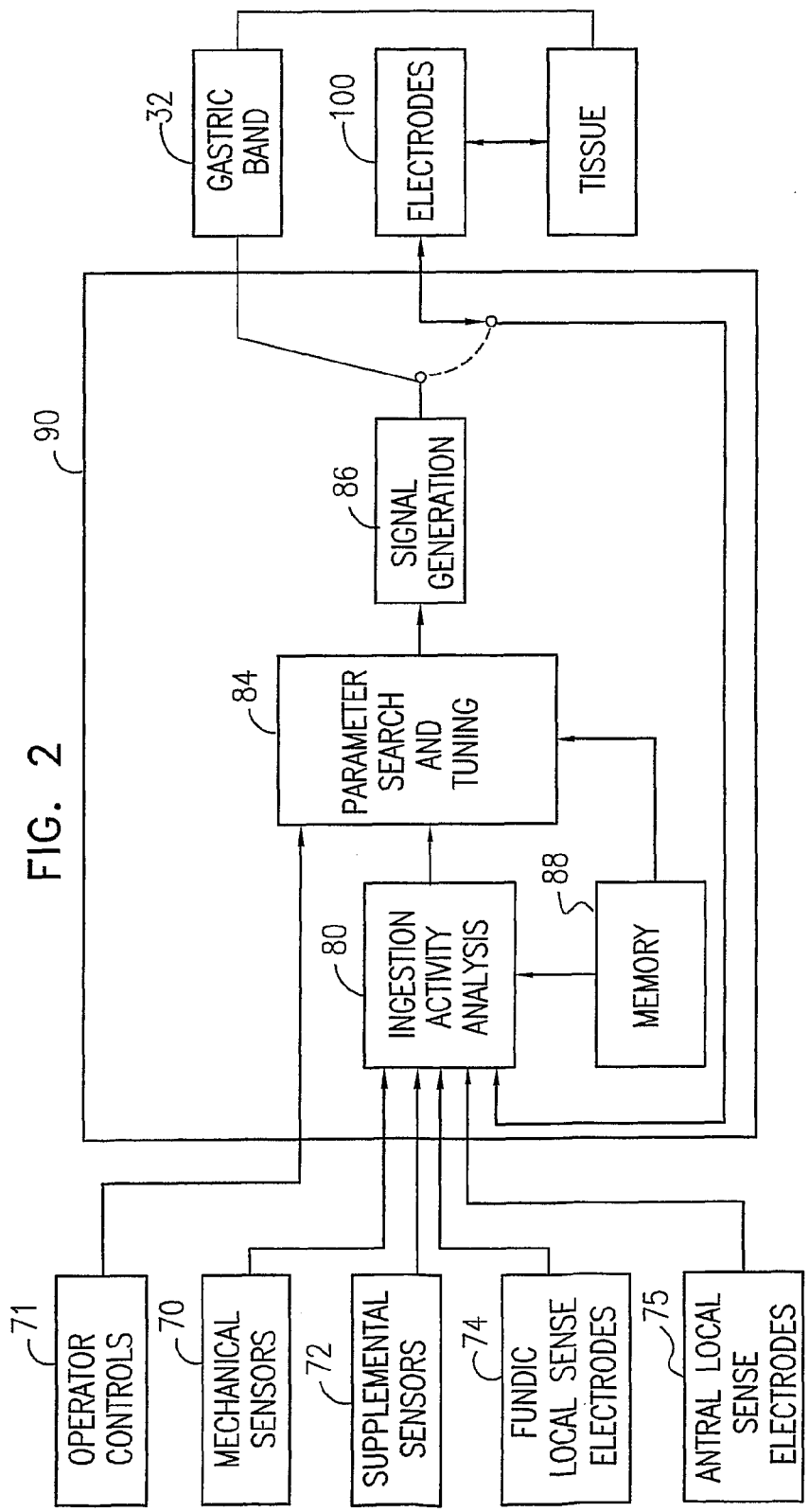
FIG. 2 is a schematic block diagram illustrating details of operation of a control unit of the apparatus of FIG. 1A or FIG. 1B, in accordance with a typical embodiment of the present invention.

FIG. 2 is a schematic block diagram illustrating details of operation of control unit 90 of apparatus 18 and 18', in accordance with an embodiment of the present invention. Control unit 90 is implanted in subject 10, and receives signals from local sense electrodes 74 and 75, and, if provided, mechanical sensors 70 and supplemental sensors 72. These sensors and electrodes are typically configured to provide an "ingestion activity analysis" block 80 of the control unit with information about food ingestion and/or the present state of the stomach.

Analysis block 80 performs the ingestion analyses described hereinbelow. In order to improve the accuracy of the analyses described hereinbelow, analysis block 80 is typically calibrated by measuring the appropriate response criteria of stomach 20 of subject 10 to various types of solid and liquid food.

For some applications, analysis block 80 stores the results of its analysis in a memory block 88 of control unit 90, and these results are later uploaded to an external computer, typically by a wireless communications link, for review by the subject's physician. Alternatively or additionally, analysis block 80 conveys results of its analysis of the inputs from mechanical sensors 70, supplemental sensors 72, and local sense electrodes 74, to a "parameter search and tuning" block 84 of control unit 90. The parameter search and tuning block adapts (a) the threshold values indicative of ingestion, by checking that an indicated ingestion event corresponds to an actual ingestion event, and (b) the threshold values indicative of food content (solid vs. liquid), by checking that an indicated food content correspondents to an actual ingested food content. For example, the parameter search and tuning block may rely on the subject to periodically verify or deny an ingestion event by using operator controls 71, or to periodically enter an indication of food content (solid vs. liquid) by using operator controls 71. In an embodiment, a false positive indication of an ingestion event causes one or more of the threshold values to be modified (e.g., increased), while a false negative may cause one or more of the threshold values to be decreased. Alternatively or additionally, an incorrect determination of food content causes one or more of the threshold values to be modified.

In an embodiment, apparatus 18 or 18' is calibrated using calibration techniques described in the above-mentioned PCT Patent Application PCT/IL05/000904, mutatis mutandis. In an embodiment, algorithms and/or pseudo-code described in the '904 application, mutatis mutandis, are used to determine the impedance and/or other thresholds described hereinabove.

In an embodiment of the present invention, control unit 90 further comprises a signal generation block 86, which drives current-application electrodes 92 to apply an electrical signal to tissue of stomach 20, or another site of the GI tract. For example, the electrical signal may include an ingestion-control signal, a satiety inducing signal, or a discomfort-inducing signal. For example, techniques may be used that are described in one or more of the following patent applications, all of which are assigned to the assignee of the present application and are incorporated herein by reference:

U.S. Provisional Patent Application 60/259,925, filed Jan. 5, 2001, entitled, "Regulation of eating habits";

PCT Patent Application PCT/IL02/00007, filed Jan. 3, 2002, entitled, "Regulation of eating habits";

PCT Patent Application PCT/IL04/000664, filed Jul. 21, 2004, entitled, "Gastrointestinal methods and apparatus for use in treating disorders and controlling blood sugar";

U.S. patent application Ser. No. 09/734,358, filed Dec. 21, 2000, entitled, "Acute and chronic electrical signal therapy for obesity," which issued as U.S. Pat. No. 6,600,953; and/or PCT Patent Application PCT/IL05/000904, filed Aug. 18, 2005, entitled, "Monitoring, analysis, and regulation of eating habits."

Additionally or alternatively, signal control unit 90 activates gastric band 32 to tighten or loosen. For example, gastric band 32 may have two or more levels of tightening, and control unit 90 may cause tightening or loosening of the gastric band, thus selecting between these tightening levels. For example, the gastric band may have two tightening levels: a relatively tight level and a relatively loose, resting level. Upon detection that an ingested food is predominantly liquid or has a significant liquid component, control unit 90 may cause tightening of the gastric band to the tighter level. After a predetermined period of time or after a determination that liquid is no longer being ingested, control unit 90 may cause loosening of the gastric band to its resting level. Alternatively, or additionally, the band may have a third, even looser tightening level. For example, upon detection that ingesta are predominantly a non-caloric liquid (such as water), control unit 90 may cause loosening of the gastric band to the loosest level, to allow unrestricted water consumption.

While FIG. 2 depicts a single control unit, this is solely by way of example. In some embodiments, two or more control units may be used, one of which controls at least gastric band 32, and another of which controls at least one of current application electrodes 92.

For some applications, one or more of the adjustable band inflation techniques are used that are described in above-referenced U.S. Pat. Nos. 5,938,669, 6,460,543, 6,453,907, and/or 6,454,699, and/or in above-referenced US Patent Application Publication 2001/0011543. Alternatively or additionally, other techniques known in the art (e.g., techniques described in one or more of the publications referred to in the Background of the Invention) are utilized for controllably adjusting the circumference of gastric band 32.

Reference is again made to FIG. 1A. In an embodiment of the present invention, user controls 71 comprise a handheld portable device, which comprises a device wireless communication module, and is configured to provide a food diary for a subject, for aiding in behavior modification related to food intake, such as weight loss. Apparatus 18 or 18' comprises an implantable wireless device communication module, which is coupled to control unit 90. The control unit is configured to drive the implantable wireless device communication module to wirelessly transmit, to the device wireless communication module, an indication of the extent to which the ingested food includes the solid food matter, as determined using one or more techniques described herein. The handheld portable device is configured to record the indication in the food diary. For some applications, in addition to transmitting the indication, control unit 90 adjusts the circumference of gastric band 32 responsively to the indication, as described hereinabove.

Reference is made to FIG. 3A, which is a flow chart illustrating an impedance algorithm 100 for detecting ingestion of solid food, in accordance with an embodiment of the present invention. Algorithm 100 is adapted to minimize false positive detections of ingestion of solid food. Algorithm 100 begins by making a tentative determination of ingestion of solid food, at a tentative solid ingestion step 101. Typically, the algorithm makes this determination based on an analysis of fundic impedance, as described hereinbelow with reference to steps 102 through 112, and/or based on an analysis of antral local sense rate, as described hereinbelow with references to steps 114 to 118. For some applications, the algorithm makes the tentative determination if either one of these analyses indicates the occurrence of ingestion, while for other applications, the algorithm makes the tentative determination only if both of these analyses indicate the occurrence of ingestion. The control unit typically performs these analyses generally in parallel, using software and/or hardware techniques for parallel execution of the algorithm, as known in the art. For some applications, all or a portion of algorithm 100 is performed using techniques described in above-mentioned U.S. Provisional Application 61/051,901, filed May 9, 2008, entitled, "Optimization of filters and parameters for eating detection."

For making the tentative determination of ingestion based on fundic impedance, algorithm 100 has as input a fundic impedance measurement 102, generated by fundic local sense electrodes 74, which are placed on or in the fundus of stomach 20 (FIGS. 1A and 1B). Fundic local sense electrodes 74 comprise two or more electrodes through which a small current is driven. A simultaneous measurement of the resultant voltage drop and/or a time constant associated therewith yields the impedance. Impedance measurement 102 is generated and inputted into the algorithm periodically, e.g., once every 100 ms. It is noted that although successive impedance measurements are generally described herein as being separated by 100 ms, this is by way of illustration and not limitation. For applications in which battery life is not a significant concern, more frequent measurement periods may be used, e.g., once every 10 ms. Alternatively, for some applications, impedance measurements are carried out approximately once every 1-10 seconds, once every 10 seconds to one minute, or once every 1-5 minutes, e.g., once every two minutes.

At a baseline calculation step 106, upon receipt of fundic impedance measurements 102, algorithm 100 uses the impedance measurements to calculate a baseline value of the fundic impedance. Algorithm 100 typically uses a slow-reacting formula for calculating the baseline value, in order to avoid having high frequency noise affect the calculation of the baseline. For example, the algorithm may use the following equation to calculate and update the baseline value:

$$B_t = [B_{t-1}*(N1*N3-1)+X_t]/(N1*N3)$$

where $B_t$ is the baseline value at time t (initialized to zero), $B_{t-1}$ is the baseline value at time t−1, N1 is a constant, e.g., 512, $X_t$ is impedance measurement 102 at time t, and N3 is a configurable parameter, typically having a value between about 1 and about 32. For example, N3 may have a value selected from 1, 2, 4, 8, 16, 22, and 32. Higher values of N3 result in slower convergences of $X_t$ to baseline $B_t$. For some applications, the algorithm instead uses Equation 2.1.1 of above-mentioned U.S. Provisional Application 61/051,901. For some applications, the algorithm corrects for baseline drift using techniques described in Section 3.1.1 of the '901 provisional application.

Typically, algorithm 100 applies a high-pass filter to impedance measurement 102, by comparing the measurement to the baseline value, at a high-pass filter step 108. Typically, the algorithm performs this comparison by subtracting the baseline value from impedance measurement 102, resulting in an impedance variance value, i.e., the extent to which the impedance measurement varies from the baseline. Upon initialization of algorithm 100, the algorithm may repeat step 106 for a certain number of periods, so as to obtain a reasonable convergence on the baseline value, prior to performing step 108 for the first time. For some applications, this repetition of step 106 is performed during each cycle through algorithm 100.

Alternatively, algorithm 100 applies a high-pass filter to impedance measurement 102 by using finite and infinite impulse response digital filter design techniques. For example, the resulting filter may take the form of a Butterworth topology or a Chebyshev topology.

Typically, at a low-pass filter step 110, algorithm 100 applies a low-pass filter to the impedance variance value, resulting in a processed impedance value. This low-pass filtering serves to smooth variations in the impedance variance value, and to filter out spurious high and low values. For example, algorithm 100 may use the following equation to perform the low-pass filtering:

$$S_t = [S_{t-1}*(2^{N4}-1)+(X_t-B_t)]/2^{N4}$$

wherein $S_t$ is the processed impedance value at time t (initialized to zero), N4 is a configurable parameter, typically having a value between about 1 and about 8, $X_t$ is impedance measurement 102 at time t, and $B_t$ is the last calculated value in step 106, as described above. For example, N4 may have a value selected from 1, 2, 3, 4, 5, 6, 7, and 8. Higher values of N4 tend to reduce false positive indications of ingestion, while lower values tend to reduce false negatives. In general, any of the values 1-8 is suitable. For some applications, the algorithm instead uses Equation 2.1.3 of above-mentioned U.S. Provisional Application 61/051,901.

Alternatively, algorithm 100 applies a low-pass filter to impedance measurement 102 by using finite and infinite impulse response digital filter design techniques. For example, the resulting filter can take the form of a Butterworth topology or a Chebyshev topology.

Algorithm 100 compares the processed impedance value to a configurable fundic increase threshold value, at a fundic impedance check step 112. The fundic increase threshold value typically is between about 2 and about 80 ohms, such as between about 30 and about 40 ohms. Because the processed impedance value represents a difference between impedance measurement 102 and the baseline value, the fundic increase threshold value is typically expressed as an absolute value (i.e., in ohms), rather than as a percentage change. If algorithm 100 finds that the processed impedance value is less than the fundic increase threshold, the algorithm waits until a new fundic impedance measurement 102 is generated, and repeats the analysis. On the other hand, if algorithm 100 finds at step 112 that the processed impedance value is greater than the fundic increase threshold, the algorithm makes a tentative determination of ingestion by the subject.

For making the tentative determination of ingestion based on antral local sense rate, algorithm 100 has as input an antral local sense measurement 114, as measured by antral local sense electrodes 75. At a rate calculation step 116, algorithm 100 calculates the rate of antral slow waves, such as by using techniques described in above-mentioned PCT Publication WO 06/018851. Algorithm 100 compares the calculated rate to a configurable antral rate decrease threshold value, at an antral sense rate check step 118. The antral rate decrease threshold value typically is between about 2.4 and about 3.33 waves per minute, such as about 2.85 waves per minute. If algorithm 100 finds that the rate is greater than the antral rate decrease threshold, the algorithm waits until a new antral local sense measurement 114 is generated, and repeats the analysis. On the other hand, if algorithm 100 finds at step 118 that the rate is less than the antral rate decrease threshold, the algorithm makes a tentative determination of ingestion by the subject.

Alternatively, and mathematically equivalently, algorithm 100 calculates the interval of the antral slow waves, which is the reciprocal of the rate. Algorithm 100 compares the calculated interval to a configurable antral interval increase threshold value, which is typically between about 18 and about 25 seconds, such as about 21 seconds. If algorithm 100 finds that the interval is less than the antral interval increase threshold, the algorithm waits until a new antral local sense measurement 114 is generated, and repeats the analysis. On the other hand, if algorithm 100 finds at step 118 that the interval is greater than the antral interval increase threshold, the algorithm makes a tentative determination of ingestion by the subject.

In general, the scope of embodiments of the present invention includes mathematically equivalent ways of practicing the embodiments, such as substituting rates for intervals or vice versa, and making appropriate changes to the algorithms.

Upon making a tentative determination of ingestion of solid food at step 101, in order to determine whether the tentative determination of ingestion is a false positive, algorithm 100 determines the duration of the period during which the processed fundic impedance value rose from baseline to the elevated value exceeding the fundic increase threshold value (as described hereinabove at step 112), and compares the duration to a configurable fundic rise duration threshold value, at a fundic impedance duration check step 120. The fundic rise duration threshold value typically is between about 0.1 and about 10 seconds, or between about 10 and about 60 seconds. If algorithm 100 finds that the duration is less than the fundic rise threshold, the algorithm interprets the tentative determination of ingestion as a false positive, at a false positive determination step 122, and repeats the method of FIG. 3A.

Alternatively, at check step 120 algorithm 100 determines the duration of the period during which the processed fundic impedance value was elevated, i.e., the period beginning when the processed fundic impedance value, when increasing, crossed a fundic impedance threshold value, and concluding when the processed fundic impedance value, when returning towards baseline, again crossed the fundic impedance threshold value. For some applications, the fundic impedance threshold value has the same value as the fundic increase threshold value described hereinabove at step 112, while for other application the fundic impedance threshold value has a value that is different from (i.e., greater or less than) the fundic increase threshold value described hereinabove at step 112. The algorithm compares the duration of elevation with the fundic rise duration threshold value, which, for this technique, is typically between about 0.1 and about 80 seconds, such as between about 2 and about 5 seconds. For some applications, the threshold value is somewhat flexible. For example, the elevated period may conclude when the processed fundic impedance value falls below a value that is greater than the fundic threshold value, such as by a certain number of ohms (e.g., between about two and about 10 ohms), or by a certain percentage of the impedance rise value (e.g., between about 5% and about 30% of the impedance change).

Typically (but not necessarily) in parallel to performing check step 120, algorithm 100 determines whether the food that has been tentatively determined to have been ingested is solid or liquid, at a solid food check step 124, as described hereinbelow with reference to algorithm 200 of FIG. 3B. If algorithm 100 finds that the ingested food was liquid, the algorithm interprets the tentative determination of solid food ingestion as a false positive at false positive determination step 122, and repeats the method of FIG. 3A.

If algorithm 100 finds, at check step 120, that the duration is greater than the fundic rise threshold, and at check step 124, that the ingested food is solid, the algorithm generates an ingestion detection signal, at an ingestion detected step 126. For some applications, algorithm 100 performs only one of the false-positive checks described hereinabove with reference to check steps 120 and 124, rather than both of these checks. For some applications in which the algorithm performs both checks, check step 120 is performed prior to, or simultaneously with, check step 124. Alternatively, for some applications, algorithm 100 interprets the tentative determination of eating as a false positive only if the algorithm finds both (a) at fundic impedance duration check step 120, that the duration is less than the fundic rise threshold, and (b) at solid food check step 124, that the ingested food is liquid. Alternatively, for some applications, algorithm 100 performs neither check step 120 nor check step 124.

FIG. 3B is a flow chart illustrating an algorithm 200 for differentiating between ingestion of solid and liquid food, in accordance with an embodiment of the present invention. As described hereinbelow, algorithm 200 includes several check steps. For some applications, the algorithm performs all of these check steps, while for other applications, the algorithm performs fewer than all of these checks steps, such as only one, two, or three of these check steps, or a combination of certain ones of the conditions. The control unit typically performs the check steps generally in parallel, using software and/or hardware techniques for parallel execution of the algorithm, as known in the art.

At a fundic impedance check step 202, algorithm 200 compares the processed fundic impedance value (determined as described hereinabove at steps 102 through 110 of algorithm 100) to a configurable fundic increase threshold value. The fundic increase threshold value typically is between about 15 and about 80 ohms. If algorithm 200 finds that the processed impedance value is less than the fundic increase threshold, the algorithm tentatively concludes that solid food was ingested, at a solid determination step 204. Otherwise, at a liquid determination step 206, the algorithm tentatively determines that liquid food was ingested, i.e., that the detection of solid food made by algorithm 100 was a false positive.

At a fundic duration check step 208, algorithm 200 determines the duration of the period during which the processed fundic impedance value rose from baseline to the elevated value that exceeds a fundic increase threshold value, and compares the duration to a configurable fundic rise duration threshold value. This calculation of the duration is performed in a similar manner to the calculation described hereinabove at step 120 of algorithm 100. The fundic increase threshold value typically is between about 15 seconds and about 5 minutes. If algorithm 200 finds that the duration is more than the fundic rise threshold, the algorithm tentatively concludes that solid food was ingested, at solid determination step 204. Otherwise, the algorithm tentatively determines that liquid food was ingested at liquid determination step 206.

Alternatively, at check step 208 algorithm 200 determines the duration of the period during which the processed fundic impedance value was elevated, i.e., the period beginning when the processed fundic impedance value, when increasing, crossed a fundic impedance threshold value, and concluding when the processed fundic impedance value, when returning towards baseline, again crossed the fundic impedance threshold value. The algorithm compares the duration of elevation with the fundic rise duration threshold value, which, for this technique, is typically between about 0.1 and about 80 seconds, such as between about 2 and about 5 seconds. For some applications, the threshold value is somewhat flexible. For example, the elevated period may conclude when the processed fundic impedance value falls below a value that is greater than the fundic threshold value, such as by a certain number of ohms (e.g., between about two and about 10 ohms), or by a certain percentage of the impedance rise value (e.g., between about 5% and about 30% of the impedance change).

At an antral impedance check step 210, the algorithm determines a processed antral impedance value, as described below, and compares the processed antral impedance value to a configurable antral increase threshold. Algorithm 200 has as input an antral impedance measurement generated by antral local sense electrodes 75, which are placed on or in the antrum of stomach 20 (FIGS. 1A and 1B). Antral local sense electrodes 75 comprise two or more electrodes through which a small current is driven. A simultaneous measurement of the resultant voltage drop and/or a time constant associated therewith yields the impedance. Algorithm 200 determines the processed antral impedance value by using the antral impedance measurement to calculate a baseline value of the antral impedance, using techniques described hereinabove with reference to baseline calculation step 106. Depending on battery life considerations, step 210 is performed either (a) generally constantly (albeit periodically), even prior to a positive determination at check step 101 of algorithm 100, or (b) only after a positive determination at check step 101. Typically, the algorithm applies one or more filters to the impedance measurement, using techniques described hereinabove with reference to filter steps 108 and 110, in order to derive a processed impedance value. The antral increase threshold value typically is between about 2 and about 30 ohms, such as between about 10 and about 20 ohms, e.g., about 20 ohms. Because the processed impedance value represents a difference between the impedance measurement and the baseline value, the antral increase threshold value is typically expressed as an absolute value (i.e., in ohms), rather than as a percentage change. If algorithm 200 finds that the antral impedance value is more than the antral increase threshold, the algorithm tentatively concludes that liquid food was ingested, at liquid determination step 206. Otherwise, the algorithm tentatively determines that solid food was ingested at solid determination step 204.

At an antral rate check step 212, algorithm 200 determines whether a substantial reduction in an antral local sense rate over a brief period of time, after which the rate returns to baseline, has occurred. For example, the period of time may have a duration of between about 1 and about 3 detected antral waves. Alternatively or additionally, the period of time may have a duration of between about 25 and about 40 seconds. If the local sense interval length is less than an interval length threshold, the algorithm tentatively concludes that solid food was ingested, at solid determination step 204. For example, the rate threshold may be between about 25% and about 75% of the baseline rate. Otherwise, the algorithm tentatively determines that liquid food was ingested at liquid determination step 206.

For some applications, algorithm 200 uses one or more of the techniques described hereinbelow for differentiating between ingestion of predominantly solid and predominantly liquid food.

In an embodiment of the present invention, check step 112 of algorithm 100, check step 202 of algorithm 200, check step 208 of algorithm 200, and/or check step 210 of algorithm 200 are alternatively calculated using impedance change (fundus or antrum, as appropriate), rather than by comparing the filtered impedance (such as described at step 110 of algorithm 100) to a threshold value. Thus, in this embodiment, high-pass filtering for removing the baseline (such as described at step 108 of algorithm 100) need not be applied. (For using this technique at step 208 of algorithm 200, the start and end points for the duration calculation are typically determined according to the impedance change.)

For some applications, the impedance change is calculated in one of the following ways:

between two defined time points. The time points are typically located at the beginning and end of a sample window that is 5 to 300 seconds long, and the impedance change is calculated by finding the difference between the impedance at the beginning and end of the sample window. Typically, the impedance change is calculated many times during an extended time period, each calculation using the same window duration, but separated in time by a period of up to about half of the duration of the window; or based on a calculated impedance value in two different time windows. The two windows are typically separated by a value that ranges from 0 seconds (i.e., the windows are contiguous) to about 300 seconds. The widths of the windows are typically between about 5 and about 300 seconds, and may be but are not necessarily identical. The calculated impedance value in each window is typically a representative value of the impedance during the corresponding time, and thus may be, for example, the maximum, minimum, or average impedance value in each window. The impedance change is then determined by calculating the difference between the representative values in the two time windows.

In both methods, crossing the threshold of change may be indicative of either solid intake or of liquid intake. For example, if the change is calculated between two time points (or windows) which are close together (for example 10 seconds apart), a crossing of the threshold is indicative of liquid. If the two time points are separated by a larger time interval, a crossing of the threshold is indicative of solid intake, since the duration of rise for liquids is shorter than that for solids. For some applications, the time points or windows and the impedance change threshold are defined differently for each of the check steps.

For some applications, in order to make the tentative determination of ingestion at step 101 of algorithm 100, the algorithm uses techniques other than those described hereinabove with reference to steps 102 through 112 and steps 114 through 118. The algorithm may use one or more of the ingestion detection techniques described in the patents, patent application publications, and patent applications incorporated herein by reference, and/or ingestion detection techniques known in the art, for making the determination of potential ingestion.

In an embodiment of the present invention, control unit 90 uses algorithm 200 of FIG. 3B for independently differentiating between solid and liquid food ingestion, rather than for enhancing the accuracy of solid food ingestion detection.

For some applications, control unit 90 is configured to have a "refractory" period, e.g., having a duration of between 0 and 120 minutes (such as in steps of 15 minutes), typically 15 minutes, following each detection of ingestion (as measured from the conclusion of application of stimulation applied in response to the detection of ingestion), during which a new detection of ingestion is not registered. Such a refractory period is of necessity applied whether the detected ingestion was actual ingestion or a false positive detection of ingestion (i.e., detection of ingestion that did not actually occur). As a result, an occurrence of actual ingestion is sometimes not detected during the refractory period of a false positive detection. The use of the techniques described herein for reducing false positives thus serves to reduce the occurrence of refractory periods induced by false positives, with a concomitant decrease in the likelihood of failing to detect actual ingestion during such false-positive-induced refractory periods.

In an embodiment of the present invention, control unit 90 determines whether ingested food is predominantly solid or predominantly liquid. In order to differentiate between liquids and solids, the control unit analyzes fundic and antral impedances measured by the fundic and antral local sense electrodes 74 and 75, respectively. The control unit determines that ingestion has occurred, using one or more of the ingestion detection techniques described herein and/or in the patents, patent application publications, and patent applications incorporated herein by reference, and/or techniques known in the art. Upon the determination of the ingestion occurrence, the control unit differentiates between ingested liquids and solids using one or more of the following techniques:

the control unit interprets a change in antral impedance vs. baseline of more than a threshold value as indicating that the ingested food is predominately liquid. For some applications, the threshold value is:
  (a) dynamically configured to be equal to: (1) a certain percentage of a change in fundic impedance measured during the current detection of ingestion, such as between about 10% and about 100%, or (2) the change in fundic impedance measured during the current detection of ingestion less a constant value, such as between about 0 and about 10 ohms, or between about 10 and about 40 ohms. Apparatus 18 or 18' comprises one or more fundic sensors, configured to be applied to a fundus of the subject, and to generate a fundic signal, and the control unit is configured to determine fundic impedance responsively to the fundic signal;
  (b) pre-configured to be equal to: (1) a certain percentage of a threshold change in fundic impedance used in the algorithm for detecting ingestion, such as between about 10% and about 100% (for example, techniques may be used for detecting ingestion that are described hereinabove at steps 102 through 112 of algorithm 100, described with reference to FIG. 3A), or (2) the threshold change in fundic impedance used in the algorithm for detecting ingestion less a constant value, such as between about 0 and about 10 ohms, or between about 10 and about 40 ohms (for example, techniques may be used for detecting ingestion that are described hereinabove at steps 102 through 112 of algorithm 100, described with reference to FIG. 3A); or
  (c) pre-configured to be equal to a constant value, which is typically between about 0 and about 10 ohms, or between about 10 and about 30 ohms.

the control unit compares the fundic impedance value to a configurable fundic increase threshold value. If the control unit finds that the impedance value is less than the fundic increase threshold, the control unit determines that solid food was ingested; otherwise, the control unit determines that liquid food was ingested.

the control unit calculates a duration of the period during which fundic impedance rises from baseline during ingestion of the food. The control unit interprets a duration greater than a first threshold value as indicating that the ingested food is predominantly solid. For example, the first threshold value may be between about 1 and about 5 minutes. A duration less than a second threshold value indicates that the ingested food is predominantly liquid. For example, the second threshold value may be between about 10 seconds and about 5 minutes, e.g., between about 10 and about 60 seconds, or between about 1 and about 5 minutes. A duration between the first and second threshold values is interpreted as being inconclusive regarding the food content.

the control unit calculates an antral local sense rate (i.e., waves per unit time) detected by antral local sense electrodes 75. The control unit interprets a substantial reduction in the rate over a brief period of time, after which the rate returns to baseline, as indicating that the ingested food is predominantly liquid. For example, the period of time may have a duration of between about 1 and about 3 detected antral waves, and the reduction may be at least between about 25% and about 75% of the baseline rate. Alternatively or additionally, the period of time may have a duration of between about 25 and about 40 seconds. A moderate reduction in the rate over a longer period of time typically indicates that the ingested food is predominantly solid. Alternatively or additionally, the control unit calculates the average rate over a brief period of time (e.g., between about 1 and about 6 detected events) and also calculates the standard deviation of the rate. The control unit interprets a low average rate over the averaged period of time as indicating that food (either solid or liquid) has been ingested. If the standard deviation is greater than a threshold value, the control unit determines that the ingested food is predominantly liquid. The inventors hypothesize that the antral local sense rate is correlated with the rate of fundic distension.

In an embodiment of the present invention, upon determining that the ingested food is predominantly liquid (such as using one or more of the techniques described herein, and typically after detecting ingestion by the subject, such as using one or more of the techniques described herein), the control unit determines whether the ingested liquid is high- or low-caloric, using one or more of the following techniques (for carrying out these techniques, the control unit comprises appropriate fundic and/or antral sensors, as described herein):

the control unit interprets a change in antral impedance vs. baseline of more than a threshold value as indicating that the ingested liquid is low-caloric. For some applications, the threshold value is:
  (a) dynamically configured to be equal to a certain percentage of a change in fundic impedance measured during the current detection of ingestion, such as between about 5% and about 100%, e.g., between about 10% and about 50%, or between about 50% and about 90%;
  (b) pre-configured to be equal to a certain percentage of a threshold change in fundic impedance used in the algorithm for detecting ingestion, such as between about 5% and about 100% (for example, techniques may be used for detecting ingestion that are described hereinabove at steps 102 through 112 of algorithm 100, described with reference to FIG. 3A);
  (c) pre-configured to be equal to a certain percentage of a threshold change in antral impedance used in the algorithm for detecting eating (e.g., at step 210 of algorithm 200, described hereinabove with reference to FIG. 3B), such as between about 20% and about 90%, e.g., between about 40% and 70%; or
  (d) pre-configured to be equal to a constant value, which is typically between about 5 and about 15 ohms, or between about 15 and about 30 ohms.

For some applications, the technique for setting the threshold (e.g., (a)-(d) above) and the parameter(s) of the technique are selected for an individual subject while he is in a clinical setting. Typically, the subject is provided with one or more food intakes (e.g., comprising food having different caloric contents), and the control unit is configured with the technique and parameter(s) of the technique which most accurately correctly determine the caloric content of the intakes.

the control unit interprets a change in fundic impedance vs. baseline of more than a threshold value as indicating that the ingested liquid is low-caloric. For some applications, the threshold value is:
- (a) dynamically configured to be equal to: (1) a certain percentage of a change in antral impedance measured during the current detection of ingestion, such as between about 50% and about 200%, or (2) the change in antral impedance measured during the current detection of ingestion plus or minus a constant value, such as between about 0 and about 30 ohms;
- (b) pre-configured to be equal to: (1) a certain percentage of a threshold change in fundic impedance used in the algorithm for detecting ingestion, such as between about 50% and about 200%, or (2) the threshold change in fundic impedance used in the algorithm for detecting ingestion less a constant value, such as between about 0 and about 10 ohms, or between about 10 and about 30 ohms;
- (b) pre-configured to be equal to: (1) a certain percentage of a threshold change in fundic impedance used in the algorithm for determining that the ingested food is predominantly liquid, such as between about 30% and about 90%, or (2) the threshold change in fundic impedance used in the algorithm for determining that the ingested food is predominantly liquid, plus or minus a constant value, such as between about 5 and about 15 ohms, or between about 15 and about 40 ohms; or
- (c) pre-configured to be equal to a constant value, which is typically between about 10 and about 25 ohms, or between about 25 and about 60 ohms.

In an embodiment of the present invention, a specific schedule of allowed food ingestion is pre-programmed by the physician into the memory, and ingestion activity analysis block 80 of control unit 90 is continuously operative to detect whether food ingestion is taking place in accordance with the programmed schedule. For some subjects, the schedule may be less strict with respect to drinking liquids or certain types of liquids (e.g., low-caloric liquids), and more strict with respect to ingesting certain types of solid food. When an exception from the schedule is detected, the processor typically actuates a signal generator to generate a signal that discourages the subject from continued ingestion. For example, the signal may include an ingestion-control signal, a satiety inducing signal, a visual, audio, or other cue, tightening of a gastric band or a discomfort-inducing signal.

The timing of the tightening of a gastric band may be selected to achieve a desired goal, including optimal weight loss, blood sugar control, and/or reduction of gastric band complications. The term "timing" in this context means one or more of: (a) the period of time between determination of liquid or solid ingestion and the tightening of a gastric band, (b) the period of time between activating one ingestion control signal and its deactivation, and (c) the timing between activation of an ingestion control signal and its termination (e.g., the period of time between inflating and deflating a gastric band). This timing may vary, for example, in relation to the allowed eating schedule. For example, when the control unit detects ingestion of solid food at a time when such ingestion is not allowed, the control unit may cause the gastric band to be tightened immediately, but when the ingestion of solid food is detected during an allowed ingestion period, the control unit may delay tightening of the gastric band for a period of time to allow sufficient nourishment for the subject. The period may vary between patients and according to a therapeutic goal. For example, the period may have a duration of between about 10 minutes and about 20 minutes.

For example, techniques may be used that are described in one or more of the following patent applications, all of which are assigned to the assignee of the present application and are incorporated herein by reference:
- U.S. Provisional Patent Application 60/259,925, filed Jan. 5, 2001, entitled, "Regulation of eating habits";
- PCT Patent Application PCT/IL02/00007, filed Jan. 3, 2002, entitled, "Regulation of eating habits";
- PCT Patent Application PCT/IL04/000664, filed entitled, "Gastrointestinal methods and apparatus for use in treating disorders and controlling blood sugar";
- U.S. patent application Ser. No. 09/734,358, filed Dec. 21, 2000, entitled, "Acute and chronic electrical signal therapy for obesity," which issued as U.S. Pat. No. 6,600,953; and/or
- PCT Patent Application PCT/IL05/000904, filed Aug. 18, 2005, entitled, "Monitoring, analysis, and regulation of eating habits."

Additionally, adjustable band inflation techniques may be used that are described in above-referenced U.S. Pat. Nos. 5,938,669, 6,460,543, 6,453,907, and/or 6,454,699, and/or in above-referenced US Patent Application Publication 2001/0011543. Alternatively or additionally, other techniques known in the art (e.g., techniques described in one or more of the publications referred to in the Background of the Invention) are utilized for controllably adjusting the circumference of gastric band 32.

In an embodiment of the present invention, if the control unit detects that the ingested food is predominantly liquid, the control unit withholds applying the signal that discourages the subject from continued ingestion. For some applications, the control unit determines whether the liquid is high- or low-caloric, such as by using the techniques described hereinabove. The control unit withholds applying the signal that discourages the subject from continued ingestion only if the liquid is determined to be low-caloric. Alternatively, the control unit does not attempt to determine whether the ingested liquid is high- or low-caloric. The control unit thus withholds applying the signal that discourages the subject from continued ingestion upon detecting that the ingested food is predominantly liquid, without making a further determination regarding the caloric content of the liquid.

Reference is now made to FIGS. 4A-C and 5A-B, which are graphs showing the results of experiments performed using apparatus similar to apparatus 18 in a single human subject who was both obese and diabetic, and analysis thereof, in accordance with an embodiment of present invention. Electrodes were implanted on the fundus for measuring fundic impedance, and electrodes were implanted on the antrum for measuring antral impedance and the rate of antral electrical activity.

Figure 4A:
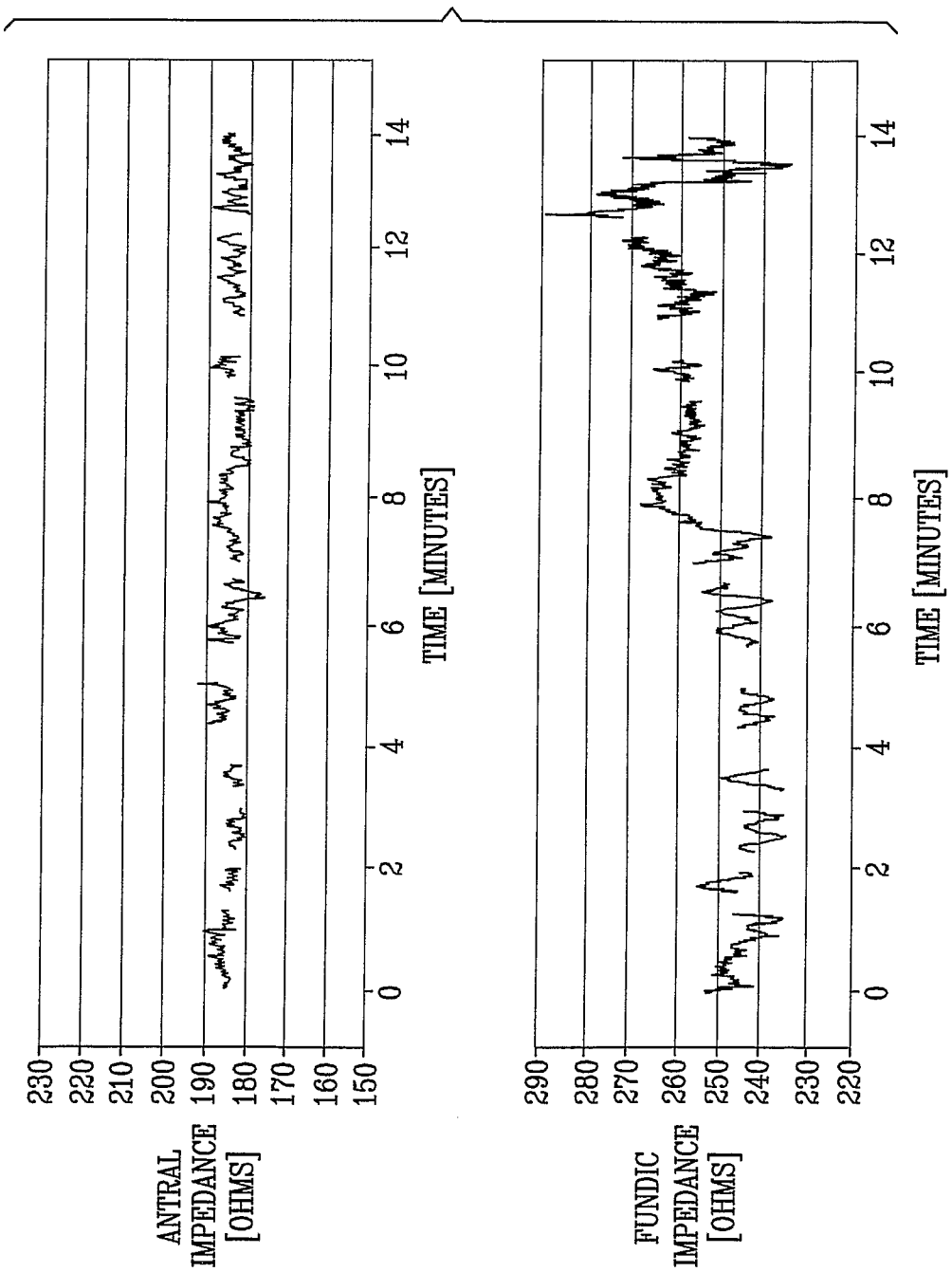

FIG. 4A shows antral and fundic impedance measured prior to, during, and after the subject ingested 250 mg of solid food (chicken and rice). Ingestion of the solid food began at approximately 7:45 minutes. (The gaps in the shown impedance signals indicate time periods during which the signals were not detected.) It can be seen that the ingestion period is distinguished by markedly increased fundic impedance (an increase of 35 ohms), but that no significant increase in antral impedance occurred (an increase of 2 ohms). As described hereinabove, in an embodiment of the present invention, the control unit interprets an occurrence of ingestion without a substantial increase in antral impedance as indicating that the ingested food is predominantly solid.

Figure 4B:
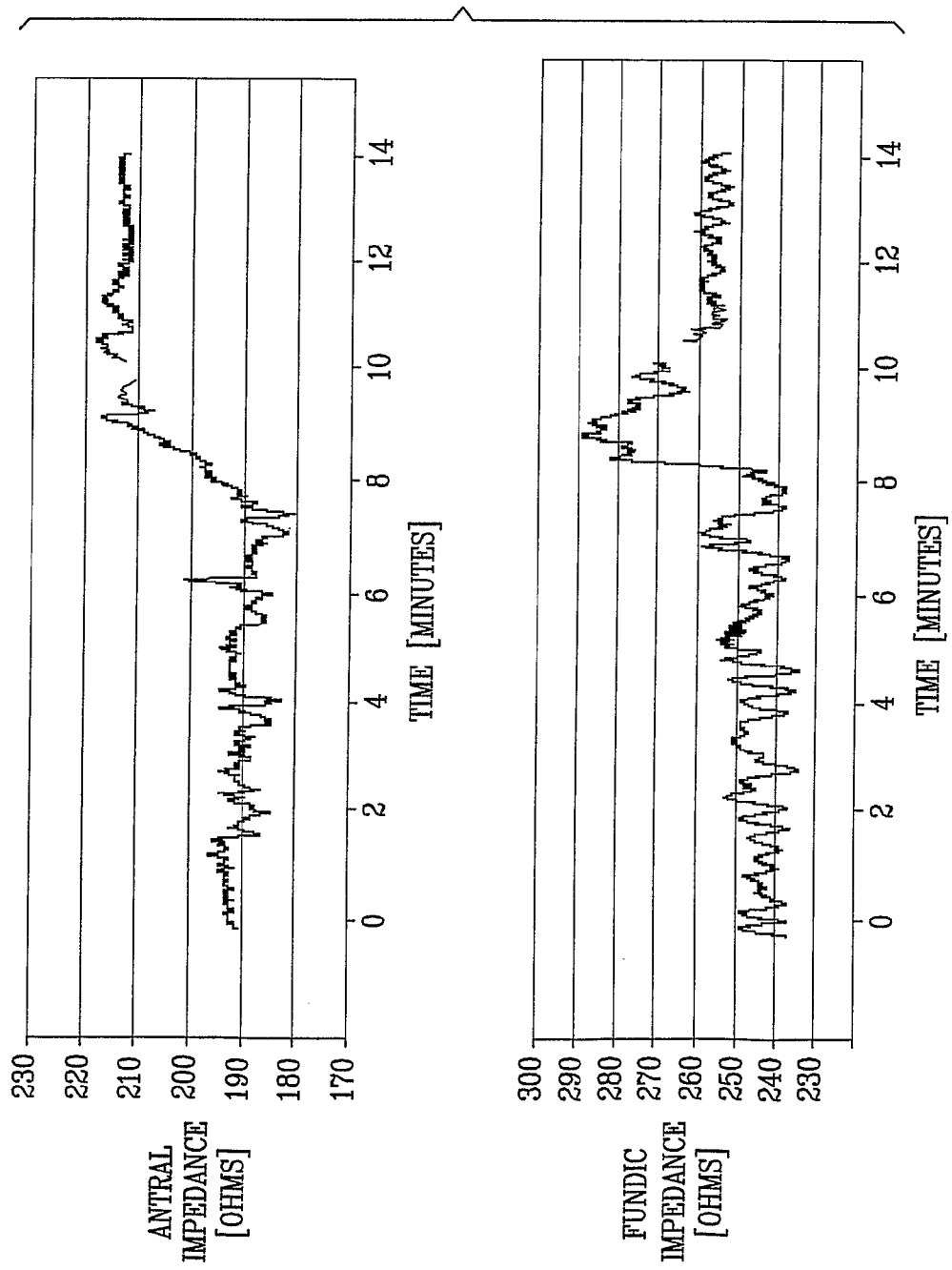

FIG. 4B shows antral and fundic impedance measured prior to, during, and after the subject drank 250 mg of non-caloric liquid (water). Ingestion of the water began at approximately 8 minutes, and concluded 12 seconds later. (The gap in the shown impedance signals indicates a time period during which the signals were not detected.) It can be seen that the drinking period is distinguished by markedly increased fundic impedance (an increase of 57 ohms) and antral impedance (an increase of 38 ohms). As described hereinabove, in an embodiment of the present invention, the control unit interprets an occurrence of ingestion accompanied by a substantial increase in antral impedance as indicating that the ingested food is predominantly liquid.

It can also be seen in FIGS. 4A and 4B that the duration of the period from the commencement of the rise in fundic impedance from the pre-ingestion level, until the return of fundic impedance to the pre-ingestion level during ingestion of solid food (FIG. 4A) was approximately 5 minutes and 50 seconds, and during ingestion of liquid food (FIG. 4B) was approximately 3 minutes. As described hereinabove, in an embodiment of the present invention, a shorter duration of the rise period of the fundic impedance signal is interpreted as indicating that the ingested food is predominantly liquid.

FIG. 4C shows antral and fundic impedance measured prior to, during, and after the subject drank 250 mg of high-caloric liquid (orange juice). Ingestion of the juice began at approximately 7:45 minutes, and concluded 18 seconds later. It can be seen that the drinking period is distinguished by markedly increased fundic impedance (an increase of 31 ohms) and antral impedance (an increase of 19 ohms). However, the increases in antral and fundic impedances were less than the increases observed when the subject drank water (FIG. 4B). As described hereinabove, in an embodiment of the present invention, the control unit interprets an occurrence of ingestion of liquid food as being one in which the ingested liquid is high-caloric when the ingestion of the liquid food is accompanied by reduced increases in antral and/or fundic impedance.

Table 1 summarizes the data shown in FIGS. 4A-C:

TABLE 1

| Food | Weight of food [gr] | Change in fundic impedance [ohms] | Change in antral impedance [ohms] | Duration of fundic impedance rise [minutes] |
| --- | --- | --- | --- | --- |
| Chicken and rice | 250 | 35 | 2 | 5:50 |
| Water | 250 | 57 | 38 | 3:00 |
| Orange juice | 250 | 31 | 19 | 2:50 |

Figure 5A:
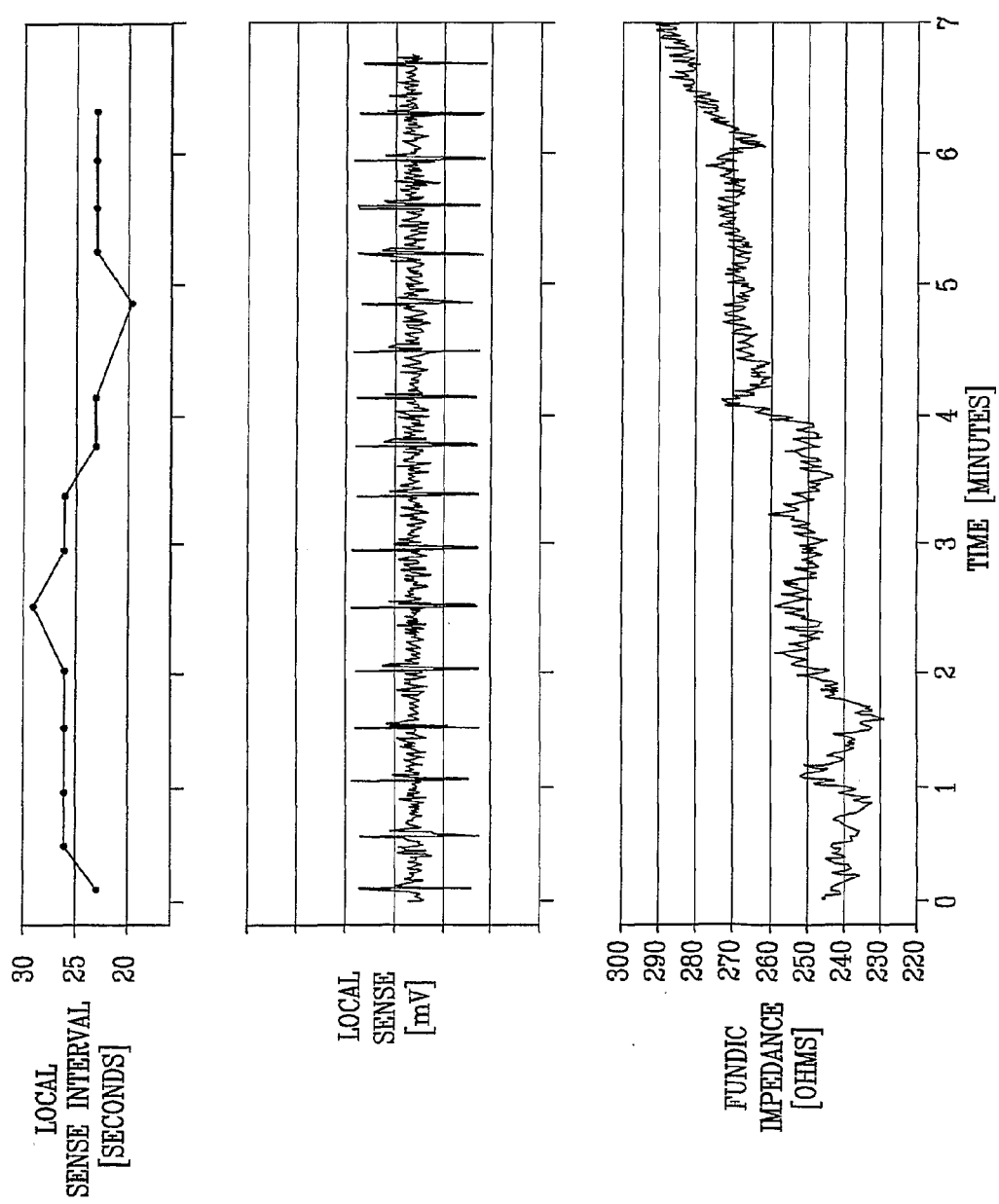
Figure 5B:
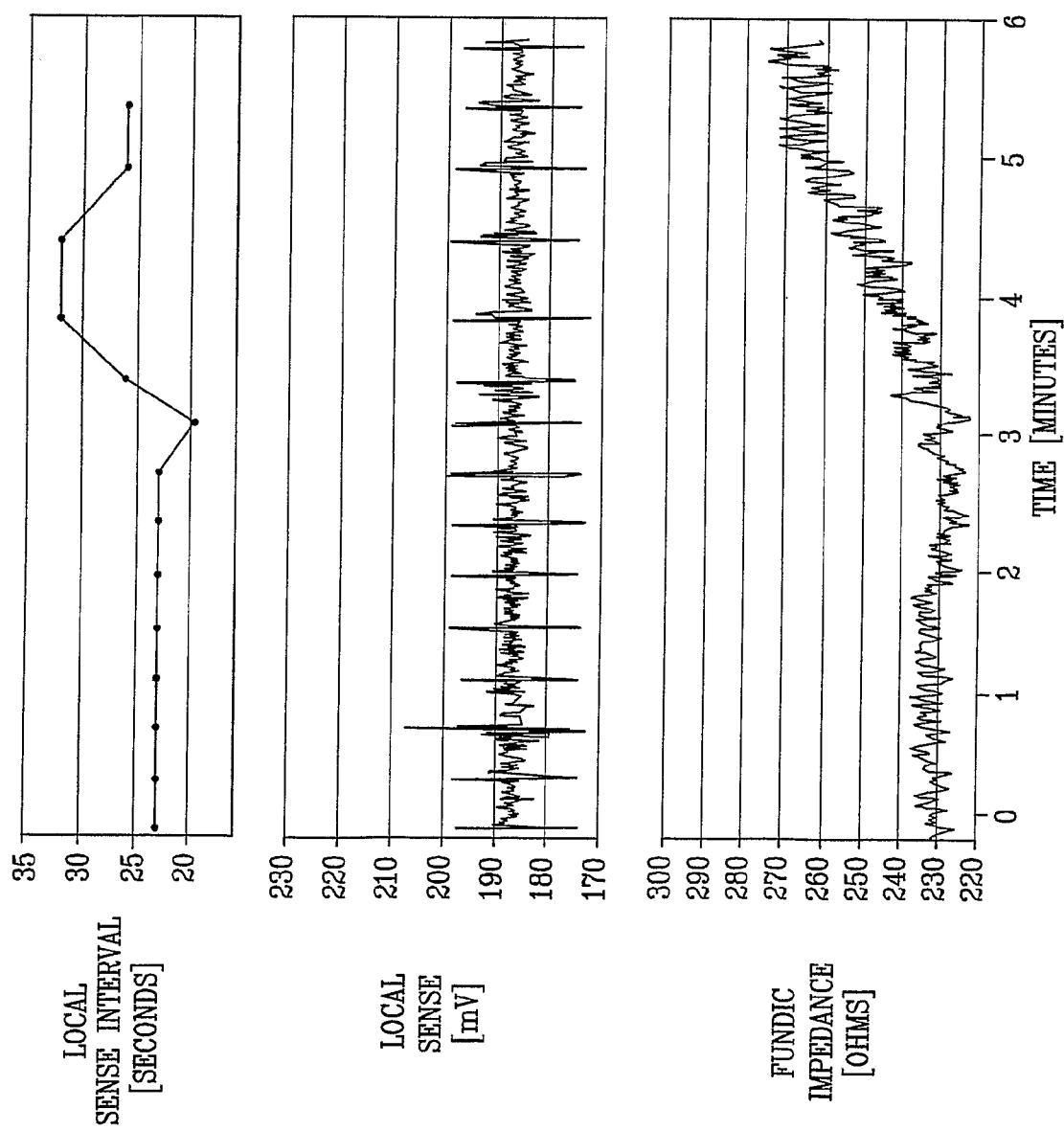

FIG. 5A shows antral local sense interval, antral electrical activity, and fundic impedance measured during solid food ingestion, measured in accordance with an embodiment of the present invention. FIG. 5B shows antral local sense interval, antral electrical activity, and fundic impedance measured during liquid food ingestion, measured in accordance with an embodiment of the present invention. The antral local sense interval for each period reflects the duration of the interval between (a) the antral electrical activity spike corresponding to the period, and (b) the following spike. Ingestion of the solid food (FIG. 5A) began at approximately 0.5 minutes, and of the liquid food (FIG. 5B) began at approximately 2.5 minutes.

As can be seen in FIGS. 5A and 5B, the antral local sense interval generally correlates with fundic impedance. During ingestion of solid food, as shown in FIG. 5A, fundic impedance increases gradually as the fundus distends slowly, and the antral local sense interval declines moderately (from typical values of about 20 seconds to typical values of about 23 seconds) and remains reduced over a relatively long period of time (about five antral spikes). In contrast, during ingestion of liquid food, as shown in FIG. 5B, fundic impedance increases quickly as the fundus distends quickly, and the antral local sense interval increases substantially (from typical values of about 20 seconds to typical values of about 32 seconds) and remains elevated for only a relatively short period of time (about one or two antral spikes). As described hereinabove, in an embodiment of the present invention, the control unit interprets a substantial reduction in the antral local sense rate (i.e., a substantial increase in antral local sense interval) over a brief period of time, after which the rate returns to baseline, as indicating that the ingested food is predominantly liquid. A moderate reduction in the rate over a longer period of time typically indicates that the ingested food is predominantly solid.

Alternatively or additionally, the control unit measures an increase in the amplitude of antral contractions, using impedance or another method. The control unit interprets an increase in the antral contraction amplitude as having the same meaning as the rate reduction described above. This technique thus allows for the substitution of a measure of reduction in antral rate with a measure of increase in antral contraction amplitude, and may be used in any of the techniques described herein which are described as using antral rate reduction, instead of or in combination with the antral rate reduction.

Figure 6A:
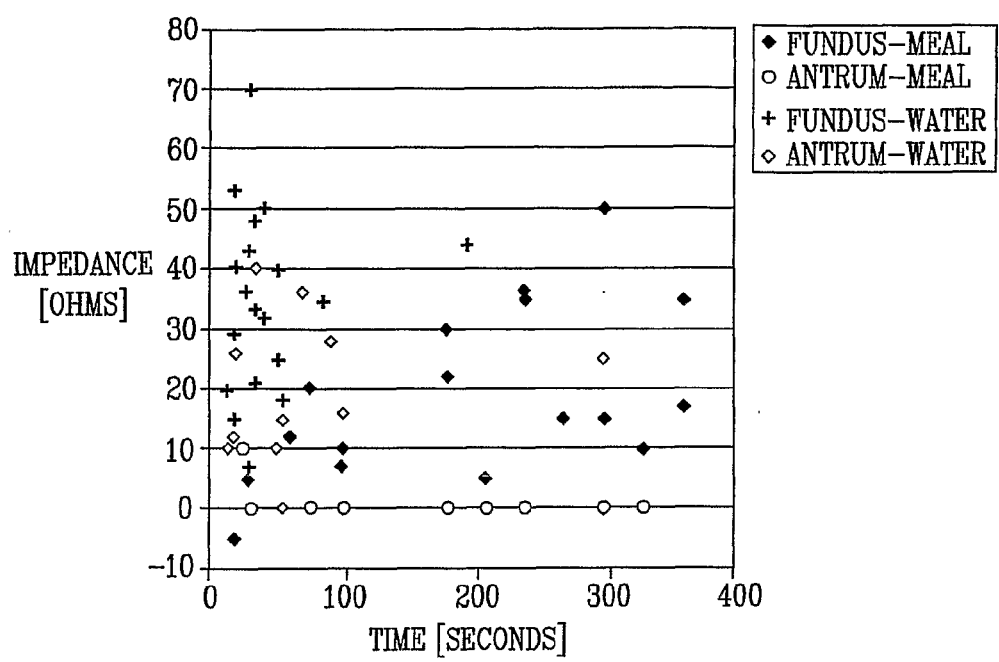
FIGS. 6A-C are graphs showing the results of an experiment on 11 human subjects, performed in accordance with an embodiment of present invention.
Figure 6B:
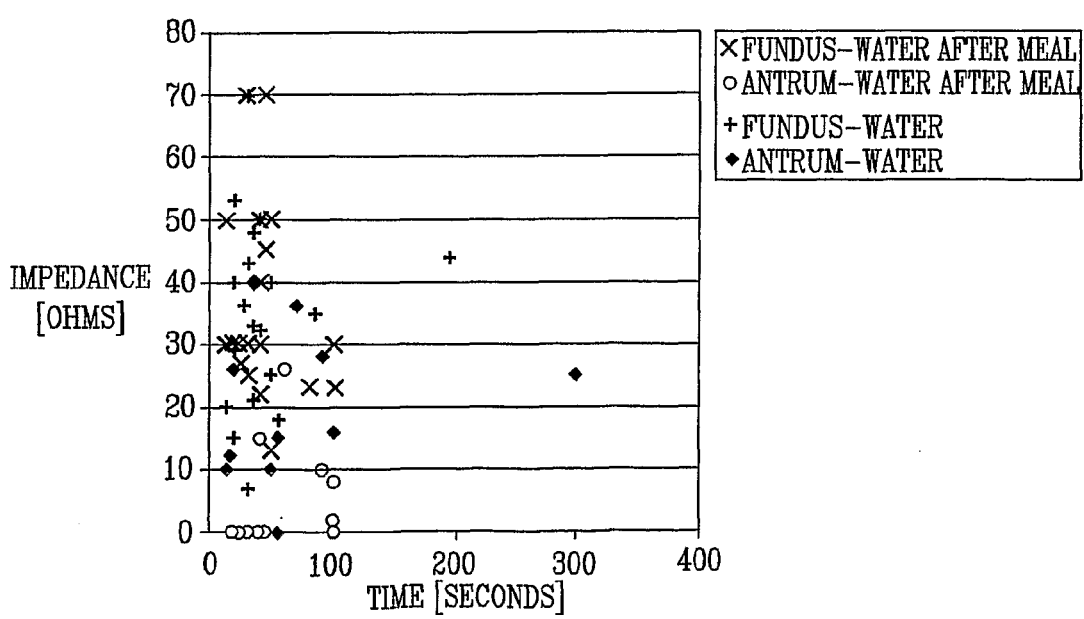
Figure 6C:
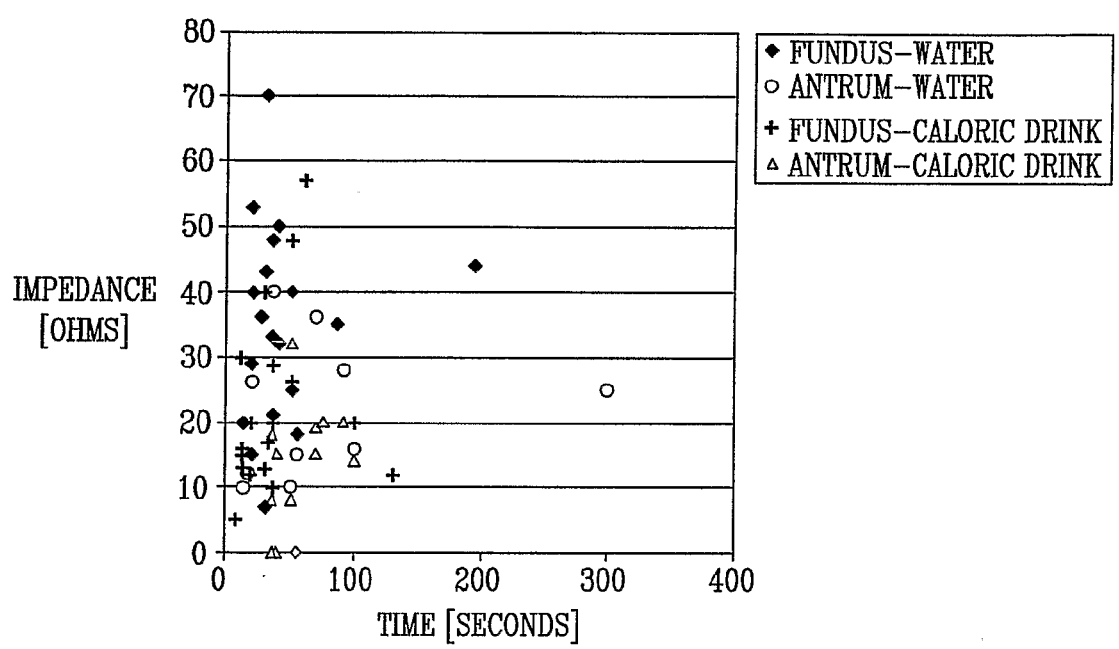

Reference is made to FIGS. 6A-C, which are graphs showing the results of an experiment on 11 human subjects who were both obese and diabetic, performed in accordance with an embodiment of present invention. Each of the subjects was implanted with apparatus similar to apparatus 18. Measurements were taken during a total of 60 separate experimental sessions for the 11 subjects. Impedance rise and rise time were measured from the commencement of the rise to peak value. During each of the sessions, one of the following three protocols was performed:

after fasting, the subject ingested a solid meal (e.g., a turkey sandwich). At least 20 minutes after the completion of the solid meal, the subject ingested 250 ml of water;

after fasting, the subject ingested 250 ml of water; or after fasting, the subject ingested 250 ml of a high-caloric liquid (e.g., orange juice).

FIG. 6A shows fundic and antral impedance measurements made at different points in time after the ingestion of food or water by a fasting subject. As can be seen in the graph, a sharp increase in antral and fundic impedance occurred within two minutes after the ingestion of water. In contrast, the antrum showed almost no reaction to the ingestion of solid food. The rise in fundic impedance after food ingestion was more gradual than after water ingestion.

FIG. 6B shows fundic and antral impedance measurements made at different points in time after the ingestion of water after fasting, and after the ingestion of water at least 20 minutes after completing a solid meal. As can be seen in the graph, fundic impedance rose sharply and quickly after water ingestion, regardless of the starting state (fasting or post-meal). The antrum, however, did not react consistently to water ingestion after a meal, but did show a sharp rise after water ingestion following fasting.

FIG. 6C shows fundic and antral impedance measurements made at different points in time after the ingestion of water or high-caloric liquid by a fasting subject. As can be seen in the graph, both the fundus and the antrum reacted similarly to high-caloric and non-caloric liquid of the same fluidity. These results may indicate that the differences in impedance for water vs. solid food observed hereinabove with reference to FIGS. 6A and 6B resulted primarily from volumetric changes in different places in the stomach, and not from the caloric content of the substance ingested.

Figure 7:
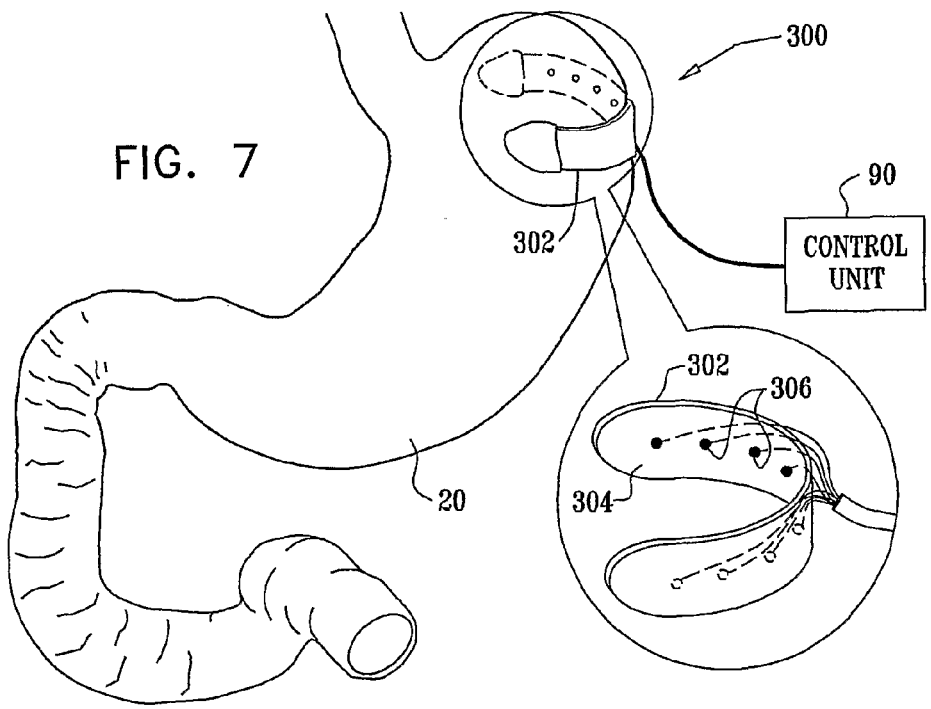
FIG. 7 is a schematic illustration of a GI tract electrode attachment device including a semi-rigid attachment element, in accordance with an embodiment of the present invention.
Figure 8:
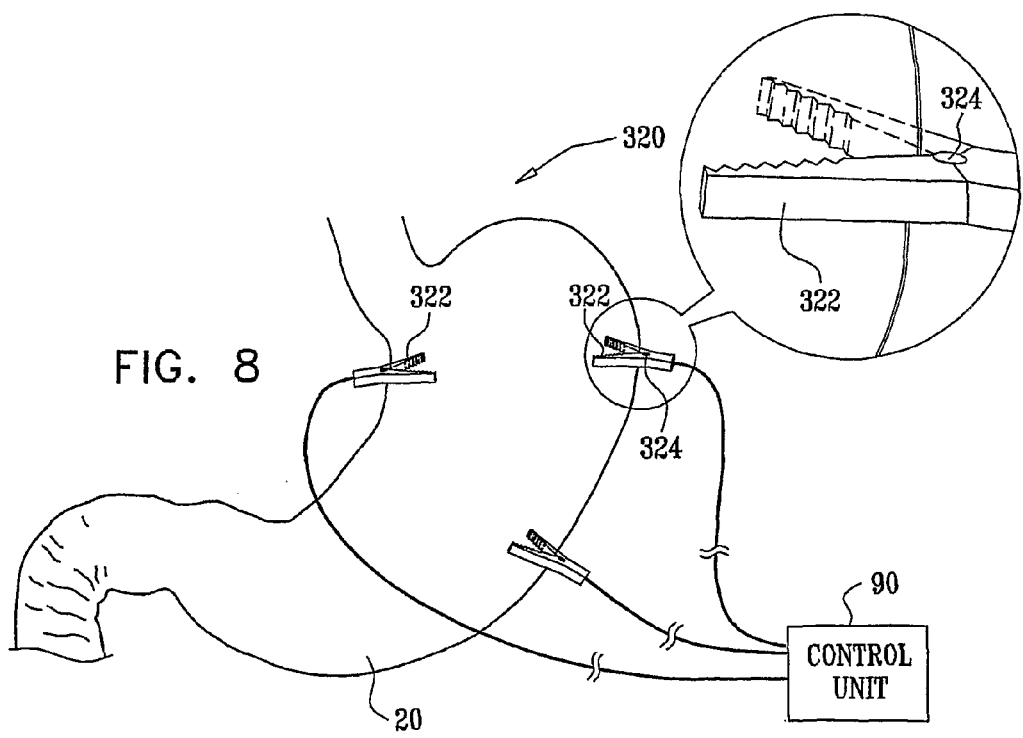
FIG. 8 is a schematic illustration of a GI tract electrode attachment device including one or more clips, in accordance with an embodiment of the present invention.
Figure 9:
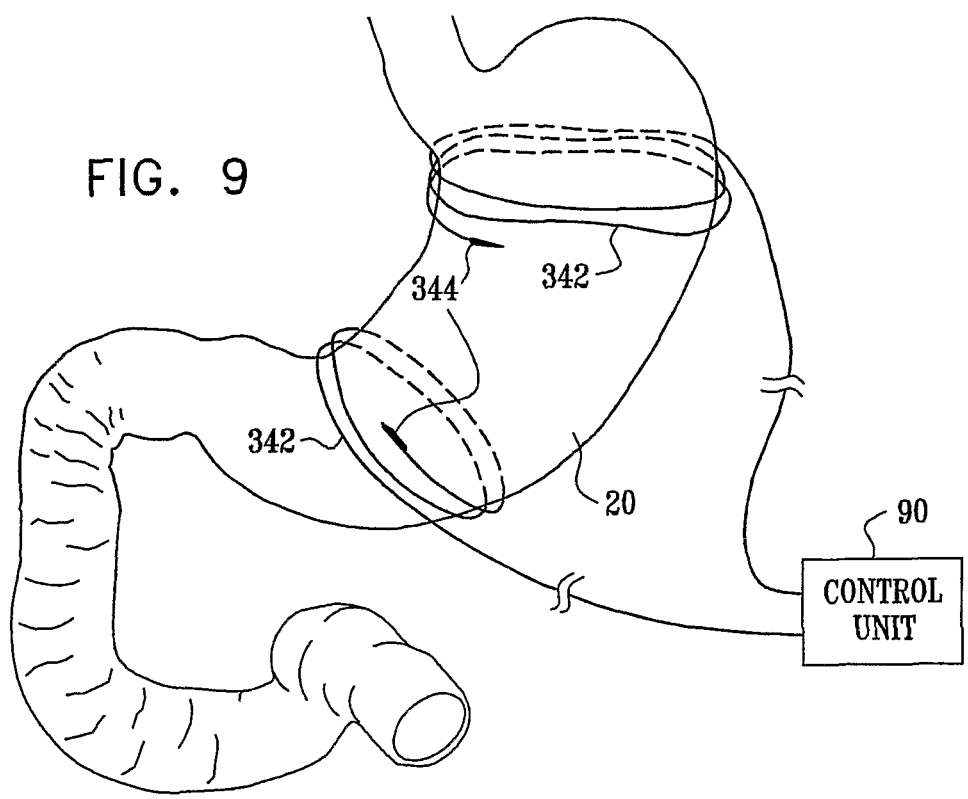
FIG. 9 is a schematic illustration of a GI tract electrode attachment device including one or more leads configured to encircle the GI tract, in accordance with an embodiment of the present invention.

Reference is made to FIGS. 7-9, which are schematic illustrations of respective GI tract electrode attachment devices, in accordance with respective embodiments of the present invention. These GI tract electrode attachment devices are configured such that attachment of the electrodes thereof applies a constrictive force to a portion of the GI tract, e.g., stomach 20, sufficient to cause a reduction in a volume of the GI tract portion, such as at least a 5%, 10%, or 20% reduction in volume, and/or a reduction in a cross-sectional area of the GI tract portion, such as least a 5%, 10%, or 20% reduction in cross-sectional area.

In the embodiment shown in FIG. 7, a GI tract electrode attachment device 300 comprises a semi-rigid attachment element 302, which is configured to surround and grasp a portion of the GI tract by applying a constrictive force thereto. For some applications, element 302 surrounds less than 360 degrees of the GI tract, e.g., less than 270 degrees, less than 180 degrees, or less than 90 degrees. A surface 304 of attachment element 302 that comes in contact with the GI tract comprises one or more electrodes 306, which may comprise, for example, one or more of fundic local sense electrodes 74, antral local sense electrodes 75, and/or current-application electrodes 92, described hereinabove with reference to FIG. 1A. Element 302 is generally stiff, with some compliance, and may comprise, for example, metal or a polymer. Although electrode attachment device 300 is shown in FIG. 7 as being applied to the fundus, for some applications, the device is applied to the antrum or body of the stomach, or to another portion of the GI tract.

In the embodiment shown in FIG. 8, a GI tract electrode attachment device 320 comprises one or more clips 322, each of which serves as one or more electrodes, and, optionally, comprises at least one spring 324 to secure the clip to tissue of the GI tract. Electrodes 324 may comprise, for example, one or more of fundic local sense electrodes 74, antral local sense electrodes 75, and/or current-application electrodes 92, described hereinabove with reference to FIG. 1A. Clips 322 are configured to apply a compressive force to the GI tract when coupling electrodes 324 thereto. For some applications, clips 322 comprise alligator clips.

In the embodiment shown in FIG. 9, a GI tract electrode attachment device 340 comprises one or more leads 342 configured to encircle the GI tract one or more times, thereby applying a constrictive force to the GI tract. Each of leads 342 comprises one or more electrodes 344. For some applications, each of the leads comprises at least two electrodes, and/or two leads encircle the GI tract at generally the same position on the GI tract (in which case, the two leads may or may not be at least partially coupled to one another, or intertwined with one another) (configuration not shown). For some applications in which device 340 comprises at least first and second leads 342, both leads encircle the GI track in the same direction (clockwise or counterclockwise), while for other applications, the first and second leads circle the GI track in opposite directions (optionally forming a mesh).

The scope of the present invention includes embodiments described in the following applications, which are assigned to the assignee of the present application and are incorporated herein by reference. In an embodiment; techniques and apparatus described in one or more of the following applications are combined with techniques and apparatus described herein:

U.S. Provisional Patent Application 60/259,925, filed Jan. 5, 2001, entitled, "Regulation of eating habits";

PCT Patent Application PCT/IL02/00007, filed Jan. 3, 2002, entitled, "Regulation of eating habits";

PCT Patent Application PCT/IL00/00132, filed Mar. 5, 2000, entitled, "Blood Glucose Level Control," and U.S. patent application Ser. No. 09/914,889 in the national stage thereof, which issued as U.S. Pat. No. 7,006,871, and U.S. patent application Ser. No. 11/318,845, which is a division thereof;

PCT Patent Application PCTIL00/00566, filed Sep. 13, 2000, entitled, "Blood Glucose Level Control," and U.S. patent application Ser. No. 10/237,263, filed Sep. 5, 2002, which is a continuation-in-part thereof;

PCT Patent Application PCT/IL03/000736, filed Sep. 4, 2003, entitled, "Blood Glucose Level Control," and U.S. patent application Ser. No. 10/526,708 in the national stage thereof, and U.S. patent application Ser. No. 10/804,560, filed Mar. 18, 2004, which is a continuation-in-part thereof;

PCT Patent Application PCT/IL04/000797, filed Sep. 5, 2004, entitled, "Blood Glucose Level Control," and U.S. patent application Ser. No. 10/570,576 in the national stage thereof;

PCT Patent Application PCT/IL04/000664, filed Jul. 21, 2004, entitled, "Gastrointestinal methods and apparatus for use in treating disorders and controlling blood sugar";

U.S. patent application Ser. No. 09/734,358, filed Dec. 21, 2000, entitled, "Acute and chronic electrical signal therapy for obesity," which issued as U.S. Pat. No. 6,600,953;

PCT Patent Application PCT/IL05/000904, filed Aug. 18, 2005, entitled, "Monitoring, analysis, and regulation of eating habits," and U.S. patent application Ser. No. 11/573,722 in the national stage thereof;

U.S. Provisional Patent Application 60/602,550, filed Aug. 18, 2004, entitled, "Monitoring, analysis, and regulation of eating habits";

PCT Patent Application PCT/IL2007/000052 to Levi et al., filed Jan. 14, 2007, entitled, "Electrode assemblies, tools, and methods for gastric wall implantation," which published as PCT Publication WO 07/080,595;

PCT Patent Application PCT/IL2006/000198 to Ben-Haim, filed Feb. 15, 2006, entitled, "Charger with data transfer capabilities," and U.S. patent application Ser. No. 11/816,574 in the national stage thereof;

PCT Patent Application PCT/IL2005/000316 to Harel et al., filed Mar. 18, 2005, entitled, "Gastrointestinal methods and apparatus for use in treating disorders and controlling blood sugar," and U.S. patent application Ser. No. 10/599,015 in the national stage thereof;

PCT Patent Application PCT/IL2004/000550 to Ben-Haim et al., filed Jun. 20, 2004, entitled, "Gastrointestinal methods and apparatus for use in treating disorders," which published as PCT Publication WO 04/112563, and U.S. patent application Ser. No. 10/561,491 in the national stage thereof;

PCT Patent Application PCT/IL2006/000204, filed Feb. 16, 2006, entitled, "Non-immediate Effects of Therapy," and U.S. patent application Ser. No. 11/884,389 in the national stage thereof;

PCT Patent Application PCT/US05/044557, filed Dec. 9, 2005, entitled, "Protein Activity Modification," and U.S. patent application Ser. No. 11/792,811 in the national stage thereof;

PCT Patent Application PCT/US06/17281, filed May 4, 2006, entitled, "Protein Activity Modification," and U.S. patent application Ser. No. 11/919,491 in the national stage thereof, and U.S. patent application Ser. No. 11/802,685, filed May 25, 2007, which is a continuation-in-part thereof;

PCT Patent Application PCT/US2006/010911 to Policker et al., filed Mar. 24, 2006, entitled, "Wireless leads for gastrointestinal tract applications," which published as PCT Publication WO 06/102626, and a US patent application filed Sep. 24, 2007 in the national stage thereof;

PCT Patent Application PCT/IL2006/000644 to Policker et al., filed Jun. 4, 2006, entitled, "GI lead implantation," which published as PCT Publication WO 06/129321;

U.S. Provisional Patent Application 60/916,919, filed May 9, 2007, entitled, "Analysis and regulation of food intake"; and/or U.S. Provisional Application 61/051,901, filed May 9, 2008, entitled, "Optimization of filters and parameters for eating detection."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
one or more antral sensors, configured to be applied to an antrum of a subject, and to generate an antral signal; and
a control unit, configured to:
detect ingestion of food by the subject,
determine antral impedance responsively to the antral signal, and
interpret a change in antral impedance vs. a as line value of less than a threshold value as indicating that the ingested food is predominantly solid.

2. no apparatus according to claim 1, further comprising:
gastrointestinal (GI) tract attachment element, configured to be coupled to a portion of a (GI)tract of a subject such that the element surrounds less than 360 degrees of the GI tract, and applies a constrictive force to the GI tract portion that causes at least a 5% reduction in a cross-sectional area of the GI tract in a vicinity of the portion; and
at least one electrode, electrically coupled to the control unit and coupled to the attachment element such that the electrode contacts the GI tract portion when the attachment element is coupled to the GI tract portion.

3. The apparatus according to claim 1, further comprising a gastric band, wherein the control unit is configured to cause tightening of the gastric band in response to a determination that the ingested food is predominantly solid.

4. The apparatus according to claim 1, wherein the control unit is configured to detect the ingestion of the food by;
making a tentative determination of ingestion of solid food by the subject, and
determining that the tentative determination is not a false positive upon determining that the ingested food is predominantly solid.

5. The apparatus according to claim 4, further comprising one or more fundic sensors, configured to be applied to a fundus of a subject, and to generate a fundic signal, wherein the control unit is configured to determine fundic impedance responsive to the fundic signal, calculate a duration of a period during which the fundic impedance rose during the tentatively-determined ingestion, and determine that the tentative determination is a false positive upon finding that the duration is less than a fundic rise duration threshold value.

6. The apparatus according to claim 1, further comprising:
an external device, which comprises a device wireless communication module; and
an implantable wireless device communication module, which is coupled to control unit,
wherein the control unit is configured to dike the implantable wireless device communication module to wirelessly transmit, to the device wireless communication module, an indication that the ingested food is predominantly solid.

7. A method comprising:
detecting ingestion of food by a subject;
determining antral impedance of antral impedance of the subject; and
interpreting a change in anti-al impedance vs. a baseline value of less than a threshold value as indicating that the ingested hand is predominantly solid.

8. Apparatus comprising:
one or more fundic sensors, configured to be applied to a fundus of a subject, and to generate a fundic signal; and
a control unit, configured to:
detect ingestion of food by the subject,
determine fundic impedance responsively to the fundic signal,
calculate a duration of it period during which the fundic impedance rose during the ingestion, and
determine that the ingested food is predominantly solid upon finding that the duration of the period is greater than a threshold value.

9. The apparatus according to claim 8, wherein the threshold value is between one and five minutes.

10. The apparatus according to claim 8, wherein the threshold value includes a first threshold value, and wherein the control unit is configured to determine that the ingested food is predominantly liquid upon finding that the duration of the period is less than a second threshold value.

11. The apparatus according to claim 10 wherein the second threshold value is between 10 seconds and five minutes.

12. The apparatus according to claim 8, further comprising a gastric band, wherein the control unit is configured to cause tightening of the gastric band in response to determining that the ingested food is predominantly solid.

13. The apparatus according to claim 8, wherein the control unit is configured to detect the ingestion of the food by:
making a tentative determination of ingestion of solid food by the subject, and
determining that the tentative determination is not a false positive upon determining that the ingested food is predominantly solid.

14. The apparatus according to claim 8, further comprising;
an external device, which comprises a device wireless communication module: and
an implantable wireless device communication module, which is coupled to control unit,
wherein the control unit is configured to drive the implantable wireless device communication module to wirelessly transmit, to the device wireless communication module, an indication that the ingested food is predominantly solid.

15. The apparatus according to claim 8, further comprising:
a gastrointestinal (GI) tract attachment element, configured to be coupled to a portion of a GI tract of a subject such that the element surrounds less than 360 degrees of the GI tract, and applies a constrictive force to the GI tract portion that causes at least a 5% reduction in a cross-sectional area of the GI tract in a vicinity of the portion; and
least one electrode, coupled to the control ant and coupled to the attachment element such that the electrode: contacts the GI tract portion when the attachment element is coupled to the GI tract portion.

16. A method comprising;
detecting ingestion of food by a subject;
determining fundic impedance of a fundus of the subject;
calculating a duration of a period during which the fundic impedance rose during the ingestion; and
determining that the ingested food is predominantly solid upon finding that the duration of the period is greater than a threshold value.

17. Apparatus comprising:
one or more antral sensors, configured to be applied m an antrum of a subject, and to generate an antral signal; and
a control unit, configured to
detect ingestion of food by the subject,
calculate an antral local sense rate responsively to the antral signal, and
determine that the ingested food is predominantly liquid upon finding that a reduction in the rate over a period of time is greater than a first threshold value, the period of time commencing during the ingestion of the food and having a period duration of less than a second threshold value.

18. The apparatus according to claim 17, wherein the period duration equals the duration at between one and three detected antral waves.

19. The apparatus according to claim 17, wherein the control unit is configured to receive an antral local sense baseline rate, and to set the first threshold value to be. between 25% and 75% of the baseline rate.

20. The apparatus according to claim 17, wherein the control unit is configured to receive an antral local sense baseline rate, and to determine that the ingested food is predominantly liquid only upon finding that the reduction in the rate over the period of time is greater than the first threshold value, and that the rate returns to the baseline rate after a conclusion of the period of time.

21. The apparatus according to claim 17, further comprising a gastric band, wherein the control unit is configured to cause loosening of the gastric hand responsively to determining that the ingested food is predominantly liquid.

22. The apparatus according to claim 17, wherein the control unit is configured to detect the ingestion of the food by:
making a tentative determination of ingestion of solid food by the subject, and
determining that the tentative determination is a false positive upon determining that the ingested food is predominantly liquid.

23. The apparatus according to claim 22 further comprising one one or more fundic sensors, configured to be applied to a fundus of a subject, and to generate fundic signal, wherein the control unit is configured to determine fundic impedance responsively to the fundic signal, calculate a duration of a period during which the fundic impedance rose during the tentatively-determined ingestion, and determine that the tentative determination is a false positive upon finding that the duration is less than a fundic rise duration threshold value.

24. The apparatus according to claim 17, further comprising:
an external device, which comprises a device wireless communication module; and
an implantable wireless device communication module, which is coupled to control unit,
wherein the control unit is configured to drive the implantable wireless device communication module to wirelessly transmit, to the device wireless communication module, an indication of the extent to which the ingested food includes solid food.

25. A method comprising;
detecting ingestion of food by a subject;
calculating an antral local sense rate of an antrum of the subject, and
determining that the ingested food is predominantly liquid upon finding that a reduction in the rate over a period of time is greater than a first threshold value, the period of time commencing during the ingestion of the food and having a period duration of less than a second threshold value.

26. Apparatus comprising:
one or more fundic sensors, configured to be applied to a fundus of a subject, and to generate a fundic signal; and
a control unit, configured to:
make a determination of ingestion of food by the subject,
determine fundic impedance responsively to the fundic signal,
calculate a maximum rise rate, expressible as a measure of resistance over a measure of time, in the fundic impedance during a least one period of the ingestion, and
determine that ingested food is liquid upon finding that the rise is at least equal to a fundic rise threshold value.

27. The apparatus according to claim 26, wherein the fundic rise threshold value is between one and 30 ohms per second.

28. The apparatus according to claim 26, further comprising a gastric band, wherein the control unit is configured to cause loosening of the gastric band responsively to determining that the digested food is liquid.

29. The apparatus according to claim 26, wherein the control unit is configured to detect the ingestion of the food by:
making a tentative determination of ingestion of solid food by the subject, and
determining that the tentative determination is a false positive upon determining that the ingested food is predominantly liquid.

30. The apparatus according to claim 26, further comprising:
an external device, which comprises a device wireless communication module; and
an implantable wireless device communication module, which is coupled to control unit,
wherein the control unit is configured to drive the implantable wireless device communication module to wirelessly transmit, to the device wireless communication module, an indication of the extent to which the ingested hand includes solid food.

31. A method comprising:
making a determination of ingestion of food by a subject;
determining fundic impedance of a fundus of the subject;

calculating a maximum rise rate, expressible as a measure of resistance over a measure of time, in the fundic impedance during at least one period of the ingestion; and determining that the ingested food is liquid upon finding that the rise is at least equal to a fundic rise threshold value.

\* \* \* \* \*

UNITED STATES PATENT AND TRADEMARK OFFICE
CERTIFICATE OF CORRECTION

PATENT NO. : 8,417,329 B2  
APPLICATION NO. : 12/599350  
DATED : April 9, 2013  
INVENTOR(S) : Shai Policker et al.

Page 1 of 1

It is certified that error appears in the above-identified patent and that said Letters Patent is hereby corrected as shown below:

On the Title Page, item (75), "Shal" should read: -- Shai --.
In the Claims
Column 35, Claim 1, line 8, "as line" should read: -- baseline --.
Column 35, Claim 2, line 1, "no" should read: -- The --.
Column 35, Claim 2, line 2, "gastrointestinal" should read: -- a gastronintestinal --.
Column 35, Claim 2, line 3, "(GI)tract" should read: -- GI tract --.
Column 35, Claim 4, line 2, "by;" should read: -- by: --.
Column 36, Claim 6, line 6, "dike" should read: -- drive --.
Column 36, Claim 7, line 3, "antral impedance" should read: -- an antrum --.
Column 36, Claim 7, line 5, "anti-al" should read: -- antral --.
Column 36, Claim 8, line 8, "it" should read: -- a --.
Column 36, Claim 11, line 1, "10" should read: -- 10, --.
Column 37, Claim 15, line 10, "least one electrode," should read:
-- at least one electrode, electrically --, and "ant" should read: -- unit --.
Column 37, Claim 15, line 11, "electrode:" should read: -- electrode --.
Column 37, Claim 16, line 1, "comprising;" should read: -- comprising: --.
Column 37, Claim 17, line 2, "m" should read: -- to --.
Column 37, Claim 18, line 2, "at" should read: -- of --.
Column 37, Claim 19, line 3, "be." should read: -- be --.
Column 37, Claim 23, line 1, "22" should read: -- 22, --.
Column 37, Claim 23, line 2, "one one" should read: -- one --.
Column 38, Claim 26, line 12, "ingested" should read: -- the ingested --.
Column 38, Claim 30, line 11, "hand" should read: -- food --.

Signed and Sealed this
Fourth Day of June, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,417,329 B2  Page 1 of 1
APPLICATION NO. : 12/599350
DATED : April 9, 2013
INVENTOR(S) : Shai Policker et al.

It is certified that error appears in the above-identified patent and that said Letters Patent is hereby corrected as shown below:

On the Title Page, item (75), "Shal" should read: -- Shai --.
In the Claims
Column 35, Line 42, Claim 1, line 8, "as line" should read: -- baseline --.
Column 35, Line 45, Claim 2, line 1, "no" should read: -- The --.
Column 35, Line 46, Claim 2, line 2, "gastrointestinal" should read: -- a gastrointestinal --.
Column 35, Line 47, Claim 2, line 3, "(GI)tract" should read: -- GI tract --.
Column 35, Line 62, Claim 4, line 2, "by;" should read: -- by: --.
Column 36, Line 15, Claim 6, line 6, "dike" should read: -- drive --.
Column 36, Line 23, Claim 7, line 3, "antral impedance" should read: -- an antrum --.
Column 36, Line 25, Claim 7, line 5, "anti-al" should read: -- antral --.
Column 36, Line 35, Claim 8, line 8, "it" should read: -- a --.
Column 36, Line 47, Claim 11, line 1, "10" should read: -- 10, --.
Column 37, Line 13, Claim 15, line 10, "least one electrode," should read:
-- at least one electrode, electrically --, and "ant" should read: -- unit --.
Column 37, Line 14, Claim 15, line 11, "electrode:" should read: -- electrode --.
Column 37, Line 17, Claim 16, line 1, "comprising;" should read: -- comprising: --.
Column 37, Line 26, Claim 17, line 2, "m" should read: -- to --.
Column 37, Line 39, Claim 18, line 2, "at" should read: -- of --.
Column 37, Line 43, Claim 19, line 3, "be." should read: -- be --.
Column 37, Line 63, Claim 23, line 1, "22" should read: -- 22, --.
Column 37, Line 64, Claim 23, line 2, "one one" should read: -- one --.
Column 38, Line 37, Claim 26, line 12, "ingested" should read: -- the ingested --.
Column 38, Line 64, Claim 30, line 11, "hand" should read: -- food --.

This certificate supersedes the Certificate of Correction issued June 4, 2013.

Signed and Sealed this
Second Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,417,329 B2  Page 1 of 1
APPLICATION NO. : 12/599350
DATED : April 9, 2013
INVENTOR(S) : Policker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 821 days.

Signed and Sealed this
First Day of September, 2015

Michelle K. Lee
*Director of the United States Patent and Trademark Office*